United States Patent [19]

Payne et al.

[11] Patent Number: 5,126,133
[45] Date of Patent: Jun. 30, 1992

[54] *BACILLUS THURINGIENSIS* ISOLATE ACTIVE AGAINST LEPIDOPTERAN PESTS, AND GENES ENCODING NOVEL LEPIDOPTERAN-ACTIVE TOXINS

[75] Inventors: Jewel Payne; August J. Sick, both of San Diego, Calif.

[73] Assignee: Mycogen Corporation, San Diego, Calif.

[21] Appl. No.: 371,955

[22] Filed: Jun. 27, 1989

[51] Int. Cl.$^5$ .......................... C12N 1/20; A01N 63/00
[52] U.S. Cl. ................................ 424/93 L; 435/69.1; 435/71.2; 435/91; 435/170; 435/122.1; 435/172.3; 435/252.3; 435/252.5; 435/320.1; 435/832; 536/27; 935/6; 935/9; 935/22; 935/59; 935/60; 935/61; 935/64; 424/93 A
[58] Field of Search .................. 435/69.1, 71.1, 91, 435/172.1, 170, 172.3, 252.1, 252.3, 252.5, 832, 320.1; 424/93; 935/6, 9, 22, 59, 60, 61, 64; 536/27

[56] References Cited

U.S. PATENT DOCUMENTS

| | | | |
|---|---|---|---|
| 4,277,564 | 7/1981 | Johnson et al. | 435/242 |
| 4,448,885 | 5/1984 | Schnepf et al. | 435/253 |
| 4,467,036 | 8/1984 | Schnepf et al. | 435/317 |
| 4,713,241 | 12/1987 | Wakisaka et al. | 424/93 |
| 4,771,131 | 9/1988 | Herrnstadt et al. | 536/27 |

OTHER PUBLICATIONS

Yamamoto et al., 1988 (Jun. 20). *Chemical Abstracts*, vol. 108 (251, Abstract No. 217068m, *Curr. Microbiol.*, 1988 171), 5–12.
Shimizu et al., 1988, *Agric Biol. Chem* 52(6): 1565–1573.
Honée et al., 1988, *NAR*, 16(13):6240.
Masson et al., 1989 (Jan. 11), *NAR*:17(1):446.
Schnepf et al., 1985, *J. Biol. Chem.*, 260(10):6264–6272.
Heierson et al., 1987, *J. Bacteriol.*, 169(3):1147–1152.
Schnepf, E. H. and H. R. Whiteley (1981) "Cloning and expression of *Bacillus thuringiensis* crystal protein in *Escherichia coli*," *Proc. Natl. Acad. Sci.* vol. 78, 5:2893–2897.

*Primary Examiner*—Richard C. Peet
*Attorney, Agent, or Firm*—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

11 Claims, 64 Drawing Sheets

```
           10         20         30         40         50         60
  1 ATGGAGATAA TGAATAATCA GAATCAATGC GTTCCTTATA ACTGTTTGAA TGATCCGACA
 61 ATTGAAATAT TAGAAGGAGA AAGAATAGAA ACTGGTTACA CCCAATAGA TATTTCCTTG
121 TCGCTAACGC AATTTCTGTT GAGTGAATTT GTCCCAGGTG CTGGGTTGT ATTAGTTTA
181 ATTGATTTAA TATGGGGGTT TGTGGGTCCC TCTCAATGGG ATGCATTTCT TGTGCAAATT
241 GAACAGTTAA TTAACCAAAG AATAGAGGAA TTCGCTAGGA ACCAAGCAAT TTCTAGATTA 310        320        330        340        350        360
301 GAAGGGCTAA GCAACCTTTA TCAAATTTAC GCAGAAGCTT TTAGAGAGTG GGAAGCAGAT
361 CCTACTAATC CAGCATTAAC AGAAGAGATG CGTATTCAGT TCAATGACAT GAACAGTGCT
421 CTTACAACCG CTATTCCTCT TTTTACAGTT CAAAATTATC AAGTACCTCT TCTATCAGTA
481 TATGTTCAAG CTGCAAATT ACATTATCG GTTTTGAGAG ATGTTTCAGT GTTTGGACAA
541 CGTTGGGAT TTGATGTAGC AACAATCAAT AGTCGTTATA ATGATTTAAC TAGGCTTATT 610        620        630        640        650        660
601 GGCACCTATA CAGATTATGC TGTACGCTGG TATAATACGG GATTAGAACG TGTATGGGGA
661 CCGGATTCTA GAGATTGGGT AAGGTATAAT CAATTTAGAA GAGAGCTAAC ACTAACTGTA
721 TTAGATATCG TTTCTCTGTT CCCGAACTAT GATAGTAGAA CGTATCCAAT TCGAACAGTT
781 TCCCAATTAA CTAGACAAAT TTATACAAAC CCAGTATTAG AAAATTTTGA TGGTAGTTTT
841 CGTGGAATGG CTCAGAGAAT AGAACAGAAT ATTAGGCAAC CACATCTTAT GGATCCCTT
```

FIGURE 1-1

```
      910        920        930        940        950        960
 901 AATAGTATAA CCATTTATAC TGATGTGCAT AGAGGCTTTA ATTATTGGTC AGGACATCAA
 961 ATAACAGCTT CTCCTGTCGG TTTGCGGGGG CCAGAATTTA CTTTCCTAG  ATATGGAACC
1021 ATGGGAAATG CTGCTCCACC CGTACTGATC TCAACTACTG GTTGGGGAT  TTTTAGAACA
1081 TTATCTTCAC CTCTTTACAG AAGAATTATA CTTGGTTCAG GCCCAAATAA TCAGAACCTG
1141 TTTGTCCTTG ATGGAACGGA ATTTTCTTTT GCCTCCCTAA CAGCCGATTT ACCTTCTACT 1210       1220       1230       1240       1250       1260
1201 ATATACAGAC AAAGGGGAAC GGTCGATTCA CTAGATGTAA TACCGCCACA GGATAAATAGT
1261 GTGCCAGCAC GTGCGGGATT TAGTCATCGA TTAAGTCATG TTACAATGCT GAGCCAAGCA
1321 GCTGGAGCAG TTTACACCTT GAGAGCTCCA ACGTTTTCTT GGCGACATCG TAGTGCTGAA
1381 TTCTCTAACC TAATTCCTTC ATCACAAATC ACACAGATAC CTTTAACAAA GTCTATTAAT
1441 CTTGGCTCTG GGACCTCTGT TGTTAAAGGA CCAGGATTTA CAGGAGGAGA TATTCTTCGA 1510       1520       1530       1540       1550       1560
1501 AGAACTTCAC CTGGCCAGAT TTCAACCTTA AGAGTGACTA TTACTGCACC ATTATCACAA
1561 AGATATCGCG TAAGAATTCG CTACGCTTCT ACTACAAATT TACAATTCCA TACATCAATT
1621 GACGGAAGAC CTATTAATCA GGGAATTTT  TCAGCAACTA TGAGTAGTGG GGGTAATTTA
1681 CAGTCCGGAA GCTTTAGGAC TGCAGGTTTT ACTACTCCGT TTAACTTTTC AAATGGATCA
1741 AGTATATTTA CGTTAAGTGC TCATGTCTTC AATTCAGGCA ATGAAGTTTA TATAGATCGA
```

FIGURE 1-2

```
           1810       1820       1830       1840       1850       1860
1801 ATTGAATTTG TTCCGGCAGA AGTAACATTT GAGGCGGAAT ATGATTTAGA AAGAGCCGCAA
1861 GAGGCGGTGA ATGCTCTGTT TACTTCTTCC AATCAACTAG GATTAAAAAC AAATGTGACG
1921 GACTATCATA TTGATCAAGT GTCCAATCTA GTCGAATGTT TATCCGGTGA ATTCTGTCTG
1981 GATGAAAAGA GAGAATGTC CGAGAAAGTC AAACATGCGA AGCGACTCAG TGATGAGCGG
2041 AATTTACTTC AAGACCCAAA CTTCAGAGGC ATCAATAGAC AACCAGACCG TGGCTGGAGA 2110       2120       2130       2140       2150       2160
2101 GGCAGTACGG ATATTACCAT CCAAGGAGGA GATGACGTAT TCAAAGAGAA TTACGTCACA
2161 CTACCGGGTA CCTTTAATGA GTGTTATCCT ACGTATCTGT ATCAAAAAAT AGATGAGTCG
2221 AAATTAAAAG CCTATACCCG TTACCAATTA AGAGGGTACA TCGAGGATAG TCAAGACTTA
2281 GAAATCTATT TAATTCGCTA CAATACAAAA CACGAAAACAG TAAATGTGCC AGGTACGGGT
2341 TCCTTATGGC CGCTTTCAGT CGAAAATCCA ATTGGAAAGT GCGGAGAACC AAATCGATGC 2410       2420       2430       2440       2450       2460
2401 GCACCACAAC TTGAATGGAA TCCTGATCTA GATTGTTCCT GCAGAGACGG GGAAAAATGT
2461 GCACATCACT CCCATCATTT CTCCTTGGAC ATTGATATTG GATGTACAGA TTTAAATGAG
2521 AACTTAGGTG TATGGGTGAT ATTCAAAATT AAGACGCCAAG ATGGTCACGC AAGACTAGGT
2581 AATCTAGAGT TTCTCGAAGA GAAACCATTA GTAGGCGAAT CGTTAGCACG CGTGAAGAGA
2641 GCGGAGAAGA AGTGGAGAGA CAAACGAGAG AAATTGCAAG TGGAAACAAA TATCGTTTAT
```

FIGURE 1-3

```
              2710       2720       2730       2740       2750       2760
2701 AAAGAGGCAA AAGAATCTGT AGATGCTTTA TTTGTGAACT CTCAATATGA TAGATTACAA
2761 GCGGATACCG ACATCGCGAT GATTCATGCG GCAGATAAAC GCGTTCATCG AATTCGAGAA
2821 GCATATCTTC CAGAGTTATC TGTAATTCCG GGTGTCAATG CGGGCATTTT TGAAGAATTA
2881 GAGGGACGTA TTTTCACAGC CTACTCTTTA TATGATGCGA GAAATGTCAT TAAAAATGGC
2941 GATTTCAATA ATGGCTTATC ATGCTGGAAC GTGAAAGGGC ATGTAGATGT AGAAGAACAA 3010       3020       3030       3040       3050       3060
3001 AACAACCACC GTTCGGTTCT TGTTGTCCCG GAATGGGAAG CAGAGGTGTC ACAAGAGGTT
3061 CGTGTCTGTC CAGGTCGTGG CTATATCCTA CGTGTTACAG CGTACAAAGA GGATATGGA
3121 GAAGGTTGCG TAACGATTCA TGAGATCGAA GACAATACAG ACGAACTGAA ATTCAGCAAC
3181 TGTGTAGAAG AGGAAGTATA TCCAAACAAC ACGGTAACGT GTAATGATTA TACTGCAAAT
3241 CAAGAAGAAT ACGGGGTGC GTACACTTCT CGTAATCGTG GATATCGTGA ATCTTATGAA 3310       3320       3330       3340       3350       3360
3301 AGTAATTCTT CCATACCAGC TGAGTATGCG CCAGTTTATG AGGAAGCATA TATAGATGA
3361 AGAAAAGAGA ATCCTTGTGA ATCTAACAGA GGATATGGGG ATTACACGCC ACTACCAGCT
3421 GGTTATGTGA CAAAGAATT AGAGTACTTC CCAGAAACCG ATAAGGTATG GATTGAGATC
3481 GGGGAAACGG AAGGAACATT CATCCGTGGAT AGCGTGGAAT TACTCCTTAT GGAGGAA*
```

Segment 1-*

FIGURE 1-4

|     | 1 | 2 | 3 | 4 | 5 | 6 | 7 | 8 | 9 | 10 | 11 | 12 | 13 | 14 | 15 |
|-----|---|---|---|---|---|---|---|---|---|----|----|----|----|----|----|
| 1   | Met | Glu | Ile | Met | Asn | Asn | Gln | Asn | Gln | Cys | Val | Pro | Tyr | Asn | Cys |
| 16  | Leu | Asn | Asp | Pro | Thr | Ile | Glu | Leu | Ile | Glu | Gly | Glu | Arg | Ile | Glu |
| 31  | Thr | Gly | Tyr | Thr | Pro | Ile | Asp | Ile | Ser | Leu | Ser | Leu | Thr | Gln | Phe |
| 46  | Leu | Leu | Ser | Glu | Phe | Val | Pro | Gly | Ala | Gly | Phe | Val | Leu | Gly | Leu |
| 61  | Ile | Asp | Leu | Ile | Trp | Gly | Phe | Ile | Gly | Pro | Ser | Gln | Trp | Asp | Ala |
| 76  | Phe | Leu | Val | Gln | Ile | Glu | Gln | Leu | Ile | Asn | Gln | Arg | Ile | Glu | Glu |
| 91  | Phe | Ala | Arg | Asn | Gln | Ala | Ile | Ser | Arg | Leu | Glu | Gly | Leu | Ser | Asn |
| 106 | Leu | Tyr | Gln | Ile | Tyr | Ala | Glu | Ser | Phe | Arg | Glu | Trp | Glu | Ala | Asp |
| 121 | Pro | Thr | Asn | Pro | Ala | Leu | Thr | Glu | Glu | Met | Arg | Ile | Gln | Phe | Asn |
| 136 | Asp | Met | Asn | Ser | Ala | Leu | Thr | Thr | Ala | Ile | Pro | Leu | Phe | Thr | Val |
| 151 | Gln | Asn | Tyr | Gln | Val | Pro | Leu | Leu | Ser | Val | Tyr | Val | Gln | Ala | Ala |
| 166 | Asn | Leu | His | Leu | Ser | Val | Leu | Arg | Asp | Val | Ser | Val | Phe | Gly | Gln |
| 181 | Arg | Trp | Gly | Phe | Asp | Ala | Ala | Thr | Ile | Asn | Ser | Arg | Tyr | Asn | Asp |
| 196 | Leu | Thr | Arg | Leu | Ile | Gly | Asn | Tyr | Thr | Asp | Tyr | Ala | Val | Arg | Trp |
| 211 | Tyr | Asn | Thr | Gly | Leu | Glu | Arg | Val | Trp | Gly | Pro | Asp | Ser | Arg | Asp |

FIGURE 2-1

| | | | | | | | | | | | | | | |
|---|---|---|---|---|---|---|---|---|---|---|---|---|---|---|
| 226 | Trp | Val | Arg | Tyr | Asn | Gln | Phe | Arg | Arg | Glu | Leu | Thr | Leu | Thr | Val |
| 241 | Leu | Asp | Ile | Val | Ser | Leu | Phe | Pro | Asn | Tyr | Asp | Ser | Arg | Thr | Tyr |
| 256 | Pro | Ile | Arg | Thr | Val | Ser | Gln | Leu | Thr | Arg | Glu | Ile | Tyr | Thr | Asn |
| 271 | Pro | Val | Leu | Glu | Asn | Phe | Asp | Gly | Ser | Phe | Arg | Gly | Met | Ala | Gln |
| 286 | Arg | Ile | Glu | Gln | Asn | Ile | Arg | Gln | Pro | His | Leu | Met | Asp | Leu | Leu |
| 301 | Asn | Ser | Ile | Thr | Ile | Tyr | Thr | Asp | Val | His | Arg | Gly | Phe | Asn | Tyr |
| 316 | Trp | Ser | Gly | His | Ile | Gln | Ile | Thr | Ala | Ser | Pro | Val | Gly | Phe | Ala | Gly |
| 331 | Pro | Glu | Phe | Thr | Arg | Pro | Phe | Arg | Tyr | Gly | Thr | Met | Gly | Asn | Ala | Ala |
| 346 | Pro | Pro | Val | Leu | Ile | Ser | Thr | Thr | Gly | Leu | Gly | Ile | Phe | Arg | Thr |
| 361 | Leu | Ser | Ser | Pro | Leu | Tyr | Arg | Arg | Ile | Ile | Leu | Gly | Ser | Gly | Pro |
| 376 | Asn | Asn | Gln | Asn | Leu | Phe | Val | Leu | Asp | Gly | Thr | Glu | Phe | Ser | Phe |
| 391 | Ala | Ser | Leu | Thr | Ala | Asp | Leu | Pro | Ser | Thr | Ile | Tyr | Arg | Gln | Arg |
| 406 | Gly | Thr | Val | Asp | Ser | Leu | Asp | Val | Ile | Pro | Pro | Gln | Asp | Asn | Ser |
| 421 | Val | Pro | Ala | Arg | Gly | Ala | Gly | Phe | Ser | His | Arg | Leu | Ser | His | Val | Thr |
| 436 | Met | Leu | Ser | Gln | Ala | Ala | Gly | Ala | Val | Tyr | Thr | Leu | Arg | Ala | Pro |

FIGURE 2-2

| | | | | | | | | | |
|---|---|---|---|---|---|---|---|---|---|
| 451 | Thr | Phe | Ser | Trp | Arg | His | Arg | Ser | Ala | Glu | Phe | Ser | Asn | Leu | Ile |
| 466 | Pro | Ser | Ser | Gln | Ile | Thr | Gln | Ile | Pro | Leu | Thr | Lys | Ser | Ile | Asn |
| 481 | Leu | Gly | Ser | Gly | Thr | Ser | Val | Val | Lys | Gly | Pro | Gly | Phe | Thr | Gly |
| 496 | Gly | Asp | Ile | Leu | Arg | Arg | Thr | Ser | Pro | Gly | Gln | Ile | Ser | Thr | Leu |
| 511 | Arg | Val | Thr | Ile | Thr | Ala | Pro | Leu | Ser | Gln | Arg | Tyr | Arg | Val | Arg |
| 526 | Ile | Arg | Tyr | Ala | Ser | Thr | Thr | Asn | Leu | Gln | Phe | His | Thr | Ser | Ile |
| 541 | Asp | Gly | Arg | Pro | Ile | Asn | Gln | Gly | Asn | Phe | Ser | Ala | Thr | Met | Ser |
| 556 | Ser | Gly | Asn | Leu | Gln | Ser | Gly | Ser | Phe | Arg | Thr | Ala | Gly | Phe |
| 571 | Thr | Thr | Pro | Phe | Asn | Phe | Ser | Asn | Gly | Ser | Ser | Val | Phe | Thr | Leu |
| 586 | Ser | Ala | His | Val | Phe | Asn | Ser | Gly | Asn | Glu | Val | Tyr | Ile | Asp | Arg |
| 601 | Ile | Glu | Phe | Val | Pro | Ala | Glu | Val | Thr | Phe | Glu | Ala | Glu | Tyr | Asp |
| 616 | Leu | Glu | Arg | Ala | Gln | Ala | Val | Asn | Ala | Leu | Phe | Thr | Ser | Ser |
| 631 | Asn | Gln | Leu | Gly | Leu | Lys | Thr | Asn | Val | Thr | Asp | Tyr | His | Ile | Asp |
| 646 | Gln | Val | Ser | Asn | Leu | Val | Glu | Cys | Leu | Ser | Gly | Glu | Phe | Cys | Leu |
| 661 | Asp | Glu | Lys | Arg | Glu | Leu | Ser | Glu | Lys | Val | Lys | His | Ala | Lys | Arg |

FIGURE 2-3

| | | | | | | | | | |
|---|---|---|---|---|---|---|---|---|---|
| 676 | Leu | Ser | Asp | Glu | Arg | Asn | Leu | Gln | Asp | Pro | Asn | Phe | Arg | Gly |
| 691 | Ile | Asn | Arg | Gln | Pro | Asp | Arg | Gly | Trp | Arg | Gly | Ser | Thr | Asp | Ile |
| 706 | Thr | Ile | Gln | Gly | Gly | Asp | Val | Phe | Lys | Glu | Asn | Tyr | Val | Thr |
| 721 | Leu | Pro | Gly | Thr | Phe | Asn | Glu | Cys | Tyr | Pro | Thr | Tyr | Leu | Tyr | Gln |
| 736 | Lys | Ile | Asp | Glu | Ser | Lys | Leu | Lys | Ala | Tyr | Thr | Arg | Tyr | Gln | Leu |
| 751 | Arg | Gly | Tyr | Ile | Glu | Asp | Ser | Gln | Asp | Leu | Glu | Ile | Tyr | Leu | Ile |
| 766 | Arg | Tyr | Asn | Thr | Lys | His | Glu | Thr | Val | Asn | Val | Pro | Gly | Thr | Gly |
| 781 | Ser | Leu | Trp | Pro | Leu | Ser | Val | Glu | Asn | Pro | Ile | Gly | Lys | Cys | Gly |
| 796 | Glu | Pro | Asn | Arg | Cys | Ala | Pro | Gln | Leu | Glu | Trp | Asn | Pro | Asp | Leu |
| 811 | Asp | Cys | Ser | Arg | Asp | Gly | Glu | Lys | Cys | Ala | His | His | Ser | His |
| 826 | His | Phe | Ser | Leu | Asp | Ile | Gly | Cys | Thr | Cys | Thr | Asp | Leu | Asn | Glu |
| 841 | Asn | Leu | Gly | Val | Trp | Ile | Phe | Lys | Ile | Lys | Thr | Gln | Asp | Gly |
| 856 | His | Ala | Arg | Leu | Gly | Asn | Leu | Glu | Phe | Leu | Glu | Glu | Lys | Pro | Leu |
| 871 | Val | Gly | Glu | Ser | Leu | Ala | Arg | Val | Lys | Arg | Ala | Glu | Lys | Lys | Trp |
| 886 | Arg | Asp | Lys | Arg | Glu | Lys | Leu | Gln | Val | Glu | Thr | Asn | Ile | Val | Tyr |

FIGURE 2-4

```
 901 Lys Glu Ala Lys Glu Ser Val Asp Ala Leu Phe Val Asn Ser Gln
 916 Tyr Asp Arg Leu Gln Ala Asp Thr Asp Ile Ala Met Ile His Ala
 931 Ala Asp Lys Arg Val His Arg Ile Arg Gln Ala Tyr Leu Pro Glu
 946 Leu Ser Val Ile Pro Gly Val Asn Ala Gly Ile Phe Glu Glu Leu
 961 Glu Gly Arg Ile Phe Thr Ala Tyr Ser Leu Tyr Asp Ala Arg Asn
 976 Val Ile Lys Asn Gly Asp Phe Asn Asn Gly Leu Ser Cys Trp Asn
 991 Val Lys Gly His Val Asp Val Glu Gln Asn Asn His Arg Ser
1006 Val Leu Val Pro Glu Trp Glu Ala Glu Val Ser Gln Glu Val
1021 Arg Val Cys Pro Gly Arg Gly Tyr Ile Leu Arg Val Thr Ala Tyr
1036 Lys Glu Gly Tyr Gly Glu Gly Cys Val Thr Ile His Glu Ile Glu
1051 Asp Asn Thr Asp Glu Leu Lys Phe Ser Asn Cys Val Glu Glu Glu
1066 Val Tyr Pro Asn Asn Thr Val Thr Cys Asn Asp Tyr Thr Ala Asn
1081 Gln Glu Glu Tyr Gly Gly Ala Tyr Thr Ser Arg Asn Arg Gly Tyr
1096 Gly Glu Ser Tyr Glu Ser Asn Ser Ser Ile Pro Ala Glu Tyr Ala
1111 Pro Val Tyr Glu Glu Ala Tyr Ile Asp Gly Arg Lys Glu Asn Pro
1126 Cys Glu Ser Asn Arg Gly Tyr Gly Asp Tyr Thr Pro Leu Pro Ala
1141 Gly Tyr Val Thr Lys Glu Leu Glu Tyr Phe Pro Glu Thr Asp Lys
1156 Val Trp Ile Glu Ile Gly Glu Thr Glu Gly Thr Phe Ile Val Asp
1171 Ser Val Glu Leu Leu Leu Met Glu Glu

Fragment 1-*
```

FIGURE 2-5

```
                    5                      10                     15                     20
Met Glu Ile Met Asn Asn Gln Asn Gln Cys Val Pro Tyr Asn Cys Leu Asn Asp Pro Thr
ATG GAG ATA ATG AAT AAT CAG AAT CAA TGC GTT CCT TAT AAC TGT TTG AAT GAT CCG ACA 25                     30                     35                     40
Ile Glu Ile Leu Glu Gly Glu Arg Ile Glu Thr Gly Tyr Thr Pro Ile Asp Ile Ser Leu
ATT GAA ATA TTA GAA GGA GAA AGA ATA GAA ACT GGT TAC ACC CCA ATA GAT ATT TCC TTG 45                     50                     55                     60
Ser Leu Thr Gln Phe Leu Leu Ser Glu Phe Val Pro Gly Ala Gly Phe Val Leu Gly Leu
TCG CTA ACG CAA TTT CTG TTG AGT GAA TTT GTC CCA GGT GCT GGG TTT GTA TTA GGT TTA 65                     70                     75                     80
Ile Asp Leu Ile Trp Gly Phe Val Gly Pro Ser Gln Trp Asp Ala Phe Leu Val Gln Ile
ATT GAT TTA ATA TGG GGG TTT GTG GGT CCC TCT CAA TGG GAT GCA TTT CTT GTG CAA ATT 85                     90                     95                     100
Glu Gln Leu Ile Asn Gln Arg Ile Glu Glu Phe Ala Arg Asn Gln Ala Ile Ser Arg Leu
GAA CAG TTA ATT AAC CAA AGA ATA GAG GAG TTC GCT AGG AAC CAA GCA ATT TCT AGA TTA
```

FIGURE 3-1

```
                      105                 110                 115                 120
Glu Gly Leu Ser Asn Leu Tyr Gln Ile Tyr Ala Glu Ala Phe Arg Glu Trp Glu Ala Asp
GAA GGG CTA AGC AAC CTT TAT CAA ATT TAC GCA GAA GCT TTT AGA GAG TGG GAA GCA GAT 125                 130                 135                 140
Pro Thr Asn Pro Ala Leu Thr Glu Glu Met Arg Ile Gln Phe Asn Asp Met Asn Ser Ala
CCT ACT AAT CCA GCA TTA ACA GAA GAG ATG CGT ATT CAG TTC AAT GAC ATG AAC AGT GCT 145                 150                 155                 160
Leu Thr Thr Ala Ile Pro Leu Phe Thr Val Gln Asn Tyr Gln Val Pro Leu Leu Ser Val
CTT ACA ACC GCT ATT CCT CTT TTT ACA GTT CAA AAT TAT CAA CCT CTT CTA TCA GTA 165                 170                 175                 180
Tyr Val Gln Ala Ala Asn Leu His Leu Ser Val Leu Arg Asp Val Ser Val Phe Gly Gln
TAT GTT CAA GCT GCA AAT TTA CAT TTA TCG GTT TTG AGA GAT GTT TCA GTG TTT GGA CAA 185                 190                 195                 200
Arg Trp Gly Phe Asp Val Ala Thr Ile Asn Ser Arg Tyr Asn Asp Leu Thr Arg Leu Ile
CGT TGG GGA TTT GAT GTA GCA ACA ATC AAT AGT CGT TAT AAT GAT TTA ACT AGG CTT ATT
```

FIGURE 3-2

```
                            205             210             215             220
Gly Thr Tyr Thr Asp Tyr Ala Val Arg Trp Tyr Asn Thr Gly Leu Glu Arg Val Trp Gly
GGC ACC TAT ACA GAT TAT GCT GTA CGC TGG TAT AAT ACG GGA TTA GAA CGT GTA TGG GGA
                            225             230             235             240
Pro Asp Ser Arg Asp Trp Val Arg Tyr Asn Gln Phe Arg Arg Glu Leu Thr Leu Thr Val
CCG GAT TCT AGA GAT TGG GTA AGG TAT AAT CAA TTT AGA AGA GAG CTA ACA CTA ACT GTA
                            245             250             255             260
Leu Asp Ile Val Ser Leu Phe Pro Asn Tyr Asp Ser Arg Thr Tyr Pro Ile Arg Thr Val
TTA GAT ATC GTT TCT CTG TTC CCG AAC TAT GAT AGT AGA ACG TAT CCA ATT CGA ACA GTT
                            265             270             275             280
Ser Gln Leu Thr Arg Glu Ile Tyr Thr Asn Pro Val Leu Glu Asn Phe Asp Gly Ser Phe
TCC CAA TTA ACT AGA GAA ATT TAT ACA AAC CCA GTA TTA GAA AAT TTT GAT GGT AGT TTT
                            285             290             295             300
Arg Gly Met Ala Gln Arg Ile Glu Gln Asn Ile Arg Gln Pro His Leu Met Asp Leu Leu
CGT GGA ATG GCT CAG AGA ATA GAA CAG AAT ATT AGG CAA CCA CAT CTT ATG GAT CTC CTT
```

FIGURE 3-3

```
                                       305                        310                        315                        320
Asn Ser Ile Thr    Ile Tyr Thr Asp Val    His Arg Gly Phe Asn    Tyr Trp Ser Gly His    Gln
AAT AGT ATA ACC    ATT TAT ACT GAT GTG    CAT AGA GGC TTT AAT    TAT TGG TCA GGA CAT    CAA 325                        330                        335                        340
Ile Thr Ala Ser    Pro Val Gly Phe Ala    Gly Pro Glu Phe Thr    Phe Pro Arg Tyr Gly    Thr
ATA ACA GCT TCT    CCT GTC GGT TTT GCG    GGG CCA GAA TTT ACT    TTT CCT AGA TAT GGA    ACC 345                        350                        355                        360
Met Gly Asn Ala    Ala Pro Pro Val Leu    Ser Ile Ser Thr Thr    Gly Leu Gly Ile Phe    Arg Thr
ATG GGA AAT GCT    GCT CCA CCC GTA CTG    TCA ATC TCA ACT ACT    GGT TTG GGG ATT TTT    AGA ACA 365                        370                        375                        380
Leu Ser Ser Pro    Leu Tyr Arg Arg Ile    Leu Gly Ile Leu Gly    Pro Asn Asn Gln Asn    Leu
TTA TCT TCA CCT    CTT TAC AGA AGA ATT    CTT GGT TCA GGC CCA    AAT AAT CAG AAC    CTG 385                        390                        395                        400
Phe Val Leu Asp    Gly Thr Glu Phe Ser    Phe Ala Ser Leu Thr    Ala Asp Leu Pro Ser    Thr
TTT GTC CTT GAT    GGA ACG GAA TTT TCT    TTT GCC TCC CTA ACA    GCC GAT TTA CCT TCT    ACT
```

FIGURE 3-4

```
                    405                     410                     415                     420
Ile Tyr Arg Gln Arg Gly Thr Val Asp Ser Leu Asp Val Ile Pro Pro Gln Asp Asn Ser
ATA TAC AGA CAA AGG GGA ACG GTC GAT TCA CTA GAT GTA ATA CCG CCA CAG GAT AAT AGT 425                     430                     435                     440
Val Pro Ala Arg Ala Gly Phe Ser His Arg Leu Ser His Val Thr Met Leu Ser Gln Ala
GTG CCA GCA CGT GCG GGA TTT AGT CAT CGA TTA AGT CAT GTT ACA ATG CTG AGC CAA GCA 445                     450                     455                     460
Ala Gly Ala Val Tyr Thr Leu Arg Ala Pro Thr Phe Ser Trp Arg His Arg Ser Ala Glu
GCT GGA GCA GTT TAC ACC TTG AGA GCT CCA ACG TTT TCT TGG CGA CAT CGT AGT GCT GAA 465                     470                     475                     480
Phe Ser Asn Leu Ile Pro Ser Ser Gln Ile Thr Gln Ile Pro Leu Thr Lys Ser Ile Asn
TTC TCT AAC CTA ATT CCT TCA TCA CAA ATC ACA CAG CCT TTA ACA AAG TCT ATT AAT 485                     490                     495                     500
Leu Gly Ser Gly Thr Ser Val Val Lys Gly Pro Gly Phe Thr Gly Gly Asp Ile Leu Arg
CTT GGC TCT GGG ACC TCT GTT GTT AAA GGA CCA GGA TTT ACA GGA GGA GAT ATT CTT CGA
```

FIGURE 3-5

```
                 505                510                515                520
Arg Thr Ser Pro Gly Gln Ile Ser Thr Leu Arg Val Thr Ile Ala Pro Leu Ser Gln
AGA ACT TCA CCT GGC CAG ATT TCA ACC TTA AGA GTG ACT ATT GCA CCA TTA TCA CAA 525                530                535                540
Arg Tyr Arg Val Arg Ile Arg Tyr Ala Ser Thr Thr Asn Leu His Thr Ser Ile
AGA TAT CGC GTA AGA ATT CGC TAC GCT TCT ACT ACA AAT TTA CAT ACA TCA ATT 545                550                555                560
Asp Gly Arg Pro Ile Asn Gln Gly Asn Phe Ser Ala Thr Met Ser Ser Gly Gly Asn Leu
GAC GGA AGA CCT ATT AAT CAG GGG AAT TTT TCA GCA ACT ATG TCA AGT GGG GGT AAT TTA 565                570                575                580
Gln Ser Gly Ser Phe Arg Thr Ala Gly Phe Thr Thr Pro Phe Asn Phe Ser Asn Gly Ser
CAG TCC GGA AGC TTT AGG ACT GCA GGT TTT ACT ACT CCG TTT AAC TTT TCA AAT GGA TCA 585                590                595                600
Ser Ile Phe Thr Leu Ser Ala His Val Phe Asn Ser Gly Asn Glu Val Tyr Ile Asp Arg
AGT ATA TTT ACG TTA AGT GCT CAT GTC TTC AAT TCA GGC AAT GAA GTT TAT ATA GAT CGA
```

FIGURE 3-6

| | | | | 605 | | | | | 610 | | | | 615 | | | | | 620 |
|---|---|---|---|---|---|---|---|---|---|---|---|---|---|---|---|---|---|---|
| Ile | Glu | Phe | Val | Pro | Ala | Glu | Val | Thr | Phe | Glu | Ala | Tyr | Asp | Leu | Glu | Arg | Ala | Gln |
| ATT | GAA | TTT | GTT | CCG | GCA | GAA | GTA | ACA | TTT | GAG | GCG | TAT | GAT | TTA | GAA | AGA | GCG | CAA |

| | | | 625 | | | | | 630 | | | | | 635 | | | | | 640 |
|---|---|---|---|---|---|---|---|---|---|---|---|---|---|---|---|---|---|---|
| Glu | Ala | Val | Asn | Ala | Leu | Phe | Thr | Ser | Asn | Gln | Leu | Gly | Leu | Lys | Thr | Asn | Val | Thr |
| GAG | GCG | GTG | AAT | GCT | CTG | TTT | ACT | TCT | AAT | CAA | CTA | GGA | TTA | AAA | ACA | AAT | GTG | ACG |

| | | | 645 | | | | | 650 | | | | | 655 | | | | | 660 |
|---|---|---|---|---|---|---|---|---|---|---|---|---|---|---|---|---|---|---|
| Asp | Tyr | His | Ile | Asp | Gln | Val | Ser | Asn | Leu | Val | Glu | Cys | Leu | Ser | Gly | Glu | Phe | Cys | Leu |
| GAC | TAT | CAT | ATT | GAT | CAA | GTG | TCC | AAT | CTA | GTC | GAA | TGT | TTA | TCC | GGT | GAA | TTC | TGT | CTG |

| | | | 665 | | | | | 670 | | | | | 675 | | | | | 680 |
|---|---|---|---|---|---|---|---|---|---|---|---|---|---|---|---|---|---|---|
| Asp | Glu | Lys | Arg | Glu | Leu | Ser | Glu | Lys | Val | Lys | His | Ala | Arg | Leu | Ser | Asp | Glu | Arg |
| GAT | GAA | AAG | AGA | GAA | TTG | TCC | GAG | AAA | GTC | AAA | CAT | GCG | CGA | CTC | AGT | GAT | GAG | CGG |

| | | | 685 | | | | | 690 | | | | | 695 | | | | | 700 |
|---|---|---|---|---|---|---|---|---|---|---|---|---|---|---|---|---|---|---|
| Asn | Leu | Leu | Gln | Asp | Pro | Asn | Phe | Arg | Gly | Ile | Asn | Arg | Gln | Pro | Asp | Arg | Gly | Trp | Arg |
| AAT | TTA | CTT | CAA | GAC | CCA | AAC | TTC | AGA | GGC | ATC | AAT | AGA | CAA | CCA | GAC | CGT | GGC | TGG | AGA |

FIGURE 3-7

```
                                705               710               715               720
Gly Ser Thr Asp Ile Thr Ile Gln Gly Asp Asp Val Phe Lys Glu Asn Tyr Val Thr
GGC AGT ACG GAT ATT ACC ATC CAA GGA GAT GAC GTA TTC AAA GAG AAT TAC GTC ACA 725               730               735               740
Leu Pro Gly Thr Phe Asn Glu Cys Tyr Pro Thr Tyr Leu Tyr Gln Lys Ile Asp Glu Ser
CTA CCG GGT ACC TTT AAT GAG TGT TAT CCT ACG TAT CTG CAA AAA ATA GAT GAG TCG 745               750               755               760
Lys Leu Lys Ala Tyr Thr Arg Tyr Gln Leu Arg Tyr Ile Glu Asp Ser Gln Asp Leu
AAA TTA AAA GCC TAT ACC CGT TAC CAA TTA AGA GGG TAC ATC GAG GAT AGT CAA GAC TTA 765               770               775               780
Glu Ile Tyr Leu Ile Arg Tyr Asn Thr Lys His Glu Thr Val Asn Val Pro Gly Thr Gly
GAA ATC TAT TTA ATT CGC TAC AAT ACA AAA CAC GAA ACA GTA AAT GTG CCA GGT ACG GGT 785               790               795               800
Ser Leu Trp Pro Leu Ser Val Glu Asn Pro Ile Gly Lys Cys Gly Glu Pro Asn Arg Cys
TCC TTA TGG CCG CTT TCA GTC GAA AAT CCA ATT GGA AAG TGC GGA GAA CCA AAT CGA TGC
```

FIGURE 3-8

|     |     |     |     |     | 805 |     |     |     |     | 810 |     |     |     | 815 |     |     |     | 820 |
| --- | --- | --- | --- | --- | --- | --- | --- | --- | --- | --- | --- | --- | --- | --- | --- | --- | --- | --- |
| Ala | Pro | Gln | Leu | Glu | Trp | Asn | Pro | Asp | Leu | Asp | Cys | Ser | Cys | Arg | Asp | Gly | Glu | Lys | Cys |
| GCA | CCA | CAA | CTT | GAA | TGG | AAT | CCT | GAT | CTA | GAT | TGT | TCC | TGC | AGA | GAC | GGG | GAA | AAA | TGT |

|     |     |     |     | 825 |     |     |     |     | 830 |     |     |     | 835 |     |     |     | 840 |
| --- | --- | --- | --- | --- | --- | --- | --- | --- | --- | --- | --- | --- | --- | --- | --- | --- | --- |
| Ala | His | Ser | His | His | Phe | Ser | Leu | Asp | Ile | Asp | Ile | Gly | Cys | Thr | Asp | Leu | Asn | Glu |
| GCA | CAT | TCC | CAT | CAT | TTC | TCC | TTG | GAC | ATT | GAT | ATT | GGA | TGT | ACA | GAT | TTA | AAT | GAG |

|     |     |     |     | 845 |     |     |     |     | 850 |     |     |     | 855 |     |     |     | 860 |
| --- | --- | --- | --- | --- | --- | --- | --- | --- | --- | --- | --- | --- | --- | --- | --- | --- | --- |
| Asn | Leu | Gly | Val | Trp | Val | Ile | Phe | Lys | Ile | Lys | Thr | Gln | Asp | Gly | His | Ala | Arg | Leu | Gly |
| AAC | TTA | GGT | GTA | TGG | GTG | ATA | TTC | AAA | ATT | AAG | ACG | CAA | GAT | GGT | CAC | GCA | AGA | CTA | GGT |

|     |     |     |     | 865 |     |     |     |     | 870 |     |     |     | 875 |     |     |     | 880 |
| --- | --- | --- | --- | --- | --- | --- | --- | --- | --- | --- | --- | --- | --- | --- | --- | --- | --- |
| Asn | Leu | Glu | Phe | Leu | Glu | Lys | Pro | Leu | Val | Gly | Glu | Ser | Leu | Ala | Arg | Val | Lys | Arg |
| AAT | CTA | GAG | TTT | CTC | GAA | AAA | CCA | TTA | GGC | GAA | TCG | TTA | GCA | CGC | GTG | AAG | AGA |

|     |     |     |     | 885 |     |     |     |     | 890 |     |     |     | 895 |     |     |     | 900 |
| --- | --- | --- | --- | --- | --- | --- | --- | --- | --- | --- | --- | --- | --- | --- | --- | --- | --- |
| Ala | Glu | Lys | Lys | Trp | Arg | Asp | Lys | Arg | Glu | Lys | Leu | Gln | Val | Glu | Thr | Asn | Ile | Val | Tyr |
| GCG | GAG | AAG | AAG | TGG | AGA | GAC | AAA | CGA | GAG | AAA | TTG | CAA | GTG | GAA | ACA | AAT | ATC | GTT | TAT |

FIGURE 3-9

```
Lys Glu Ala Lys Ser Val Asp Ala Leu Phe Val Asn Ser Gln Tyr Asp Arg Leu Gln
AAA GAG GCA AAA TCT GTA GAT GCT TTA TTT GTG AAC TCT CAA TAT GAT AGA TTA CAA
            905             910             915             920

Ala Asp Thr Asp Ile Ala Met Ile His Ala Ala Asp Lys Arg Val His Arg Ile Arg Glu
GCG GAT ACC GAC ATC GCG ATG ATT CAT GCA GCA GAT AAA CGC GTT CAT CGA ATT CGA GAA
        925             930             935             940

Ala Tyr Leu Pro Glu Leu Ser Val Ile Pro Gly Val Asn Ala Gly Ile Phe Glu Glu Leu
GCA TAT CTT CCA GAG TTA TCT GTA ATT CCG GGT GTC AAT GCG GGC ATT TTT GAA GAA TTA
        945             950             955             960

Glu Gly Arg Ile Phe Thr Ala Tyr Ser Leu Tyr Asp Ala Arg Asn Val Ile Lys Asn Gly
GAG GGA CGT ATT TTC ACA GCC TAC TCT TTA TAT GAT GCG AGA AAT GTC ATT AAA AAT GGC
        965             970             975             980

Asp Phe Asn Asn Gly Leu Ser Cys Trp Asn Val Lys Gly His Val Asp Val Glu Glu Gln
GAT TTC AAT AAT GGC TTA TCA TGC TGG AAC GTG AAA GGG CAT GTA GAT GTA GAA GAA CAA
        985             990             995            1000
```

FIGURE 3-10

```
                                         1005                             1010                              1015                              1020
Asn Asn His Arg Ser Val Leu Val Val Pro Glu Trp Glu Ala Glu Val Ser Gln Glu Val
AAC AAC CAC CGT TCG GTT CTT GTT GTC CCG GAA TGG GAA GCA GAG GTG TCA CAA GAG GTT 1025                             1030                              1035                              1040
Arg Val Cys Pro Gly Arg Gly Tyr Ile Leu Arg Val Thr Ala Tyr Lys Glu Gly Tyr Gly
CGT GTC TGT CCA GGT CGT GGC TAT ATC CTA CGT GTT ACA GCG TAC AAA GAG GGA TAT GGA 1045                             1050                              1055                              1060
Glu Gly Cys Val Thr Ile His Glu Ile Glu Asp Asn Thr Asp Glu Leu Lys Phe Ser Asn
GAA GGT TGC GTA ACG ATT CAT GAG ATC GAA GAC AAT ACA GAC GAA CTG AAA TTC AGC AAC 1065                             1070                              1075                              1080
Cys Val Glu Glu Val Tyr Pro Asn Asn Thr Val Thr Cys Asn Asp Tyr Thr Ala Asn
TGT GTA GAG GAG GTA TAT CCA AAC AAC ACG GTA ACG TGT AAT GAT TAT ACT GCA AAT 1085                             1090                              1095                              1100
Gln Glu Tyr Gly Gly Ala Tyr Thr Ser Arg Asn Arg Gly Tyr Gly Glu Ser Tyr Glu
CAA GAA TAC GGG GGT GCG TAC ACT TCT CGT AAT CGT GGA TAT GGT GAA TCT TAT GAA
```

FIGURE 3-11

```
                    1105                    1110                    1115                    1120
Ser Asn Ser Ser Ile Pro Ala Glu Tyr Ala Pro Val Tyr Glu Ala Tyr Ile Asp Gly
AGT AAT TCT TCC ATA CCA GCT GAG TAT GCG CCA GTT TAT GAG GCA TAT ATA GAT GGA 1125                    1130                    1135                    1140
Arg Lys Glu Asn Pro Cys Glu Ser Asn Arg Gly Tyr Gly Asp Tyr Thr Pro Leu Pro Ala
AGA AAA GAG AAT CCT TGT GAA TCT AAC AGA GGA TAT GGG GAT TAC ACG CCA CTA CCA GCT 1145                    1150                    1155                    1160
Gly Tyr Val Thr Lys Glu Leu Glu Tyr Phe Pro Glu Thr Asp Lys Val Trp Ile Glu Ile
GGT TAT GTG ACA AAA GAA TTA GAG TAC TTC CCA GAA ACC GAT AAG GTA TGG ATT GAG ATC 1165                    1170                    1175
Gly Glu Thr Glu Gly Thr Phe Ile Val Asp Ser Val Glu Leu Leu Leu Met Glu Glu
GGG GAA ACG GAA GGA ACA TTC ATC GTG GAT AGC GTG GAA TTA CTC CTT ATG GAG GAA
```

FIGURE 3-12

```
                  10         20         30         40         50         60
   1   ATGGAAATAA ATAATCAAAA CCAATGTGTG CCTTACAATT GTTTAAGTAA TCCTAAGGAG
  61   ATAATATTAG GCGAGGAAAG GCTAGAAACA GGGAATACTG TAGCAGACAT TTCATTAGGG
 121   CTTATTAATT TTCTATATTC TAATTTTGTA CCAGGAGGAG GATTTATAGT AGTTTACTA
 181   GAATTAATT GGGGATTAT AGGGCCTTCG CAATGGGATA TTTTTTTAGC TCAAATTGAG
 241   CAATTGATTA GTCAAAGAAT AGAAGAATTT GCTAGGAATC AGGCAATTTC AAGATTGGAG 310        320        330        340        350        360
 301   GGGCTAAGCA ATCTTTATAA GGTCTATGTT AGAGCGTTTA GCGACTGGGA GAAAGATCCT
 361   ACTAATCCTG CTTTAAGGGA AGAAATGCCT ATACAATTTA ATGACATGAA TAGTGCTCTC
 421   ATAACGGCTA TTCCACTTTT TAGAGTTCAA AATTATGAAG TTGCTCTTTT ATCTGTATAT
 481   GTTCAAGCCG CAAACTTACA TTTATCTATT TTAAGGGATG TTTCAGTTTT CGGAGAAAGA
 541   TGGGGATATG ATACAGCGAC TATCAATAAT CGCTATAGTG ATCTGACTAG CCTTATTCAT 610        620        630        640        650        660
 601   GTTTATACTA ACCATTGTGT GGATACGTAT AATCAGGGAT TAAGGCCGTTT GGAAGGTCGT
 661   TTTCTTAGCG ATTGGATTGT ATATAATCGT TTCCGGAGAC AATTGACAAT TTCAGTATTA
 721   GATATTGTTG CGTTTTTTCC AAATTATGAT ATTAGAACAT ATCCAATTCA AACAGCTACT
 781   CAGCTAACGA GGGAAGTCTA CCTTTTATTA ATGAAAATCT TTCTCCTGCA
 841   GCAAGCTATC CAACCTTTTC AGCTGCTGAA AGTGCTATAA TTAGAAGTCC TCATTTAGTA
```

FIGURE 4-1

```
       910        920        930        940        950        960
 901 GACTTTTTAA ATAGCTTTAC CATTTATACA GATAGTCTGG CACGTTATGC ATATTGGGGA
 961 GGGCACTTGG TAAATTCTTT CCGCACAGGA ACCACTACTA ATTTGATAAG ATCCCCTTTA
1021 TATGGAAGGG AAGGAAATAC AGAGCGCCCC GTAACTATTA CCGCATCACC TAGCGTACCA
1081 ATATTTAGAA CACTTTCATA TATTACAGGC CTTGACAATT CAAATCCTGT AGCTGGAATC
1141 GAGGGAGTGG AATTCCAAAA TACTATAAGT AGAAGTATCT ATCGTAAAAG CGGTCCAATA 1210       1220       1230       1240       1250       1260
1201 GATTCTTTTA GTGAATTACC ACCTCAAGAT GCCAGGCGTAT CTCCTGCAAT TGGGTATAGT
1261 CACCGTTTAT GCCATGCAAC ATTTTTAGAA CGGATTAGTG GACCAAGAAT AGCAGGCACC
1321 GTATTTCTT GGACACACCG TAGTGCCAGC CCTACTAATG AAGTAAGTCC ATCTAGAATT
1381 ACACAAATTC CATGGGTAAA GGCGCATACT CTTGCATCTG GTGCCTCCGT CATTAAAGGT
1441 CCTGGATTA CAGGTGGAGA TATTCTGACT AGGAATAGTA TGGGCGAGCT GGGGACCTTA 1510       1520       1530       1540       1550       1560
1501 CGAGTAACCT TCACAGGAAG ATTACCACAA AGTTATTATA TACGTTTCCG TTATGCTTCG
1561 GTAGCAAATA GGAGTGGTAC ATTTAGATAT TCACAGCCAC CTTCGTATGG AATTTCATTT
1621 CCAAAAACTA TGGACGCAGG TGAACCACTA ACATCTCGTT CGTTCGCTCA TACAACACTC
1681 TTCACTCCAA TAACCTTTTC ACGAGCTCAA GAAGAATTTG ATCTATACAT CCAATCGGGT
1741 GTTTATATAG ATCGAATTGA ATTTATACCG GTTACTGCAA CATTTGAGGC AGAATATGAT
```

FIGURE 4-2

```
          1810       1820       1830       1840       1850       1860
1801 TTAGAAAGAG CGCAAAAGGT GGTGAATGCC CTGTTTACGT CTACAAACCA ACTAGGCTA
1861 AAAACAGATG TGACGGATTA TCATATTGAT CAGGTATCCA ATCTAGTTGC GTGTTTATCG
1921 GATGAATTTT GTCTGGATGA AAAGAGAGAA TTGTCCGAGA AAGTTAAACA TGCAAAGCGA
1981 CTCAGTGATG AGCGGAATTT ACTTCAAGAT CCAAACTTCA GAGGGATCAA TAGGCAACCA
2041 GACCGTGGCT GGAGAGAAG  TACGGATATT ACTATCCAAG GAGGAGATGA CGTATTCAAA 2110       2120       2130       2140       2150       2160
2101 GAGAATTACG TTACGCTACC GGGTACCTTT GATGAGTGCT ATCCAACGTA TTTATATCAA
2161 AAAATAGATG AGTCGAAATT AAAGCCTAT  ACCCGTTATC AATTAAGAGG GTATATCGAA
2221 GATAGTCAAG ACTTAGAAAT CTATTAATT  CGTTACAATG CAAAACACGA AATAGTAAAT
2281 GTACCAGGTA CAGGAAGTTT ATGGCCTCTT TCTGTAGAAA ATCAAATTGG ACCTTGTGGA
2341 GAACCGAATC GATGCGCGCC ACACCCTTGA TGGAATCCTG ATTACACTG  TTCCTGCAGA 2410       2420       2430       2440       2450       2460
2401 GACGGGGAAA AATGTGCACA TCATTCTCAT CATTTCTCTT TGGACATTGA TGTTGGATGT
2461 ACAGACTTAA ATGAGGACTT AGTGTATGG  GTGATATTCA AGATTAAGAC GCAAGATGGC
2521 CACGCACGAC TAGGGAATCT AGAGTTCTC  GAAGAGAAAC CATTATTAGG AGAAGCACTA
2581 GCTCGTGTGA AAAGAGCGGA GAAAAATGG  AGAGACAAAC GCGAAACATT ACAATTGGAA
2641 ACAACTATCG TTTATAAAGA GGCAAAAGAA TCTGTAGATG CTTTATTTGT AAACTCTCAA
```

FIGURE 4-3

```
          2710       2720       2730       2740       2750       2760
2701 TATGATAGAT TACAAGCGGA TACGAACATC GCGATGATTC ATGCGGCAGA TAAACGCGTT
2761 CATAGAATTC GAGAAGCGTA TCTGCCGGAG CTGTCTGTGA TTCCGGGTGT CAATGCGGCT
2821 ATTTTGAAG  AATTAGAAGA GCGTATTTTC ACTGCATTTT CCCTATATGA TGCGAGAAAT
2881 ATTATTAAAA ATGGCGATTT CAATAATGGC TTATTATGCT GGAACGTGAA AGGGCATGTA
2941 GAGGTAGAAG AACAAAACAA TCACCGTTCA GTCCTGGTTA TCCCAGAATG GGAGGCAGAA 3010       3020       3030       3040       3050       3060
3001 GTGTCACAAG AGGTTCGTGT CTGTCCAGGT CGTGGCTATA TCCTTCGTGT TACAGCGTAC
3061 AAAGAGGGAT ATGGAGAAGG TTGCGTAACG ATCCATGAGA TCGAGAACAA TACAGACGAA
3121 CTGAAATTCA ACAACTGTGT AGAAGAGGAA GTATATCCAA ACAACACGGT AACGTGTATT
3181 AATTATACTG CGACTCAAGA AGAATATGAG GGTACGTACA CTTCTCGTAA TCGAGGATAT
3241 GACGAAGCCT ATGGTAATAA CCCTTCCGTA CCAGCTGATT ATGCGTCAGT CTATGAAGAA 3310       3320       3330       3340       3350       3360
3301 AAATCGTATA CAGATAGACG AAGAGAGAAT CCTTGTGAAT CTAACAGAGG ATATGGAGAT
3361 TACACCAC   TACCAGCTGG TTATGTAACA AAGGAATTAG AGTACTTCCC AGAGACCGAT
3421 AAGGTATGGA TTGAGATTGG AGAAACAGAA GGAACATTCA TCGTGGACAG CGTGGAATTA
3481 CTCCTTATGG AGGAA*

Segment 140-3634
```

FIGURE 4-4

|     |     |     | 5   |     |     |     |     | 10  |     |     |     |     | 15  |     |
| --- | --- | --- | --- | --- | --- | --- | --- | --- | --- | --- | --- | --- | --- | --- |
| 1   | Met | Glu | Ile | Asn | Asn | Gln | Cys | Val | Pro | Tyr | Asn | Cys | Leu |
| 16  | Ser | Asn | Pro | Lys | Glu | Ile | Leu | Gly | Glu | Arg | Leu | Glu | Thr |
| 31  | Gly | Asn | Thr | Val | Ala | Asp | Ile | Ser | Leu | Ile | Asn | Phe | Leu |
| 46  | Tyr | Ser | Asn | Phe | Pro | Gly | Gly | Phe | Ile | Val | Gly | Leu | Leu |
| 61  | Glu | Leu | Ile | Trp | Gly | Phe | Ile | Gly | Pro | Trp | Asp | Ile | Phe |
| 76  | Leu | Ala | Gln | Ile | Glu | Leu | Gln | Leu | Ser | Gln | Arg | Ile | Glu | Phe |
| 91  | Ala | Arg | Asn | Gln | Ala | Ile | Ser | Arg | Leu | Gly | Leu | Ser | Asn | Leu |
| 106 | Tyr | Lys | Val | Tyr | Val | Arg | Ala | Phe | Ser | Asp | Trp | Glu | Lys | Asp | Pro |
| 121 | Thr | Asn | Pro | Ala | Leu | Arg | Glu | Glu | Met | Arg | Ile | Gln | Phe | Asn | Asp |
| 136 | Met | Asn | Ser | Ala | Leu | Ile | Thr | Ala | Ile | Pro | Leu | Phe | Arg | Val | Gln |
| 151 | Asn | Tyr | Glu | Val | Ala | Leu | Leu | Ser | Val | Tyr | Val | Gln | Ala | Ala | Asn |
| 166 | Leu | His | Leu | Ser | Ile | Leu | Arg | Asp | Val | Ser | Val | Phe | Gly | Glu | Arg |
| 181 | Trp | Gly | Tyr | Asp | Thr | Ala | Thr | Ile | Asn | Asn | Arg | Tyr | Ser | Asp | Leu |
| 196 | Thr | Ser | Leu | Ile | His | Val | Tyr | Thr | Asn | His | Cys | Val | Asp | Thr | Tyr |
| 211 | Asn | Gln | Gly | Leu | Arg | Arg | Leu | Glu | Gly | Arg | Phe | Leu | Ser | Asp | Trp |

FIGURE 5-1

| | | | | | | | | | |
|---|---|---|---|---|---|---|---|---|---|
| 226 | Ile | Val | Tyr | Asn | Arg | Phe | Arg | Gln | Leu | Thr | Ile | Ser | Val | Leu |
| 241 | Asp | Ile | Val | Ala | Phe | Phe | Pro | Asn | Tyr | Asp | Ile | Arg | Thr | Tyr | Pro |
| 256 | Ile | Gln | Thr | Ala | Thr | Gln | Leu | Thr | Arg | Glu | Val | Tyr | Leu | Asp | Leu |
| 271 | Pro | Phe | Ile | Asn | Glu | Asn | Leu | Ser | Pro | Ala | Ser | Tyr | Pro | Thr |
| 286 | Phe | Ser | Ala | Ala | Glu | Ser | Ala | Ile | Ile | Arg | Ser | Pro | His | Leu | Val |
| 301 | Asp | Phe | Leu | Asn | Ser | Phe | Thr | Tyr | Thr | Asp | Ser | Leu | Ala | Arg |
| 316 | Tyr | Ala | Tyr | Trp | Gly | Gly | His | Leu | Val | Asn | Ser | Phe | Arg | Thr | Gly |
| 331 | Thr | Thr | Asn | Leu | Ile | Arg | Ser | Pro | Leu | Tyr | Gly | Arg | Glu | Gly |
| 346 | Asn | Thr | Glu | Arg | Pro | Val | Thr | Ile | Thr | Ala | Ser | Pro | Ser | Val | Pro |
| 361 | Ile | Phe | Arg | Thr | Leu | Ser | Tyr | Ile | Thr | Gly | Leu | Asp | Asn | Ser | Asn |
| 376 | Pro | Val | Ala | Gly | Ile | Glu | Gly | Val | Glu | Phe | Gln | Asn | Thr | Ile | Ser |
| 391 | Arg | Ser | Ile | Tyr | Arg | Lys | Ser | Gly | Pro | Ile | Asp | Ser | Phe | Ser | Glu |
| 406 | Leu | Pro | Pro | Gln | Asp | Ala | Ser | Val | Ser | Pro | Ala | Ile | Gly | Tyr | Ser |
| 421 | His | Arg | Leu | Cys | His | Ala | Thr | Phe | Leu | Glu | Arg | Ile | Ser | Gly | Pro |
| 436 | Arg | Ile | Ala | Gly | Thr | Val | Phe | Ser | Trp | Thr | His | Arg | Ser | Ala | Ser |

FIGURE 5-2

| | | | | | | | | | |
|---|---|---|---|---|---|---|---|---|---|
| 451 | Pro | Thr | Asn | Glu | Val | Ser | Pro | Ser | Arg | Ile | Thr | Gln | Ile | Pro | Trp |
| 466 | Val | Lys | Ala | His | Thr | Leu | Ala | Ser | Gly | Ala | Ser | Val | Ile | Lys | Gly |
| 481 | Pro | Gly | Phe | Thr | Gly | Asp | Ile | Leu | Thr | Arg | Asn | Ser | Met | Gly |
| 496 | Glu | Leu | Gly | Thr | Leu | Arg | Val | Thr | Phe | Thr | Gly | Arg | Leu | Pro | Gln |
| 511 | Ser | Tyr | Tyr | Ile | Arg | Phe | Arg | Tyr | Ala | Ser | Val | Ala | Asn | Arg | Ser |
| 526 | Gly | Thr | Phe | Arg | Tyr | Ser | Gln | Pro | Pro | Ser | Tyr | Gly | Ile | Ser | Phe |
| 541 | Pro | Lys | Thr | Met | Asp | Ala | Gly | Glu | Pro | Leu | Thr | Ser | Arg | Ser | Phe |
| 556 | Ala | His | Thr | Thr | Leu | Phe | Thr | Pro | Ile | Thr | Phe | Ser | Arg | Ala | Gln |
| 571 | Glu | Phe | Asp | Leu | Tyr | Ile | Gln | Ser | Gly | Val | Tyr | Ile | Asp | Arg |
| 586 | Ile | Glu | Phe | Ile | Pro | Val | Thr | Ala | Thr | Phe | Glu | Ala | Glu | Tyr | Asp |
| 601 | Leu | Glu | Arg | Ala | Gln | Lys | Val | Asn | Ala | Leu | Phe | Thr | Ser | Thr |
| 616 | Asn | Gln | Leu | Gly | Leu | Lys | Thr | Asp | Val | Thr | Asp | Tyr | His | Ile | Asp |
| 631 | Gln | Val | Ser | Asn | Leu | Val | Ala | Cys | Leu | Ser | Asp | Glu | Phe | Cys | Leu |
| 646 | Asp | Glu | Lys | Arg | Glu | Leu | Ser | Glu | Lys | Val | Lys | His | Ala | Lys | Arg |
| 661 | Leu | Ser | Asp | Glu | Arg | Asn | Leu | Leu | Gln | Asp | Pro | Asn | Phe | Arg | Gly |

FIGURE 5-3

```
676  Ile Asn Arg Gln Pro Asp Arg Gly Trp Arg Gly Ser Thr Asp Ile
691  Thr Ile Gln Gly Gly Asp Asp Val Phe Lys Glu Asn Tyr Val Thr
706  Leu Pro Gly Thr Phe Asp Glu Cys Tyr Pro Thr Leu Tyr Gln
721  Lys Ile Asp Glu Ser Lys Leu Ala Tyr Thr Arg Tyr Gln Leu
736  Arg Gly Tyr Ile Glu Asp Ser Gln Asp Leu Glu Ile Tyr Leu Ile
751  Arg Tyr Asn Ala Lys His Glu Ile Val Asn Val Pro Gly Thr Gly
766  Ser Leu Trp Pro Leu Ser Val Glu Asn Gln Ile Gly Pro Cys Gly
781  Glu Pro Asn Arg Cys Ala Pro His Leu Glu Trp Asn Pro Asp Leu
796  His Cys Ser Cys Arg Asp Gly Gln Lys Cys Ala His His Ser His
811  His Phe Ser Leu Asp Ile Asp Val Gly Cys Thr Asp Leu Asn Glu
826  Asp Leu Gly Val Trp Val Ile Phe Lys Ile Lys Thr Gln Asp Gly
841  His Ala Arg Leu Gly Asn Leu Glu Phe Leu Glu Lys Pro Leu
856  Leu Gly Glu Ala Leu Ala Arg Val Lys Arg Ala Glu Lys Lys Trp
871  Arg Asp Lys Arg Glu Gln Thr Leu Gln Leu Thr Thr Ile Val Tyr
886  Lys Glu Ala Lys Gly Glu Ser Val Asp Ala Leu Phe Val Asn Ser Gln
```

FIGURE 5-4

```
901  Tyr Asp Arg Leu Gln Ala Asp Thr Asn Ile Ala Met Ile His Ala
916  Ala Asp Lys Arg Val His Arg Ile Arg Glu Ala Tyr Leu Pro Glu
931  Leu Ser Val Ile Pro Gly Val Asn Ala Ala Ile Phe Glu Glu Leu
946  Glu Glu Arg Ile Phe Thr Ala Phe Ser Leu Tyr Asp Ala Arg Asn
961  Ile Ile Lys Asn Gly Asp Phe Asn Asn Gly Leu Leu Cys Trp Asn
976  Val Lys Gly His Val Glu Val Gln Asn Asn His Arg Ser
991  Val Leu Val Ile Pro Glu Trp Glu Ala Glu Val Ser Gln Glu Val
1006 Arg Val Cys Pro Gly Arg Gly Tyr Ile Leu Arg Val Thr Ala Tyr
1021 Lys Glu Gly Tyr Gly Glu Gly Cys Val Thr Ile His Glu Ile Glu
1036 Asn Asn Thr Asp Glu Leu Lys Phe Ser Asn Cys Val Glu Glu Glu
1051 Val Tyr Pro Asn Asn Thr Val Thr Cys Ile Asn Tyr Thr Ala Thr
1066 Gln Glu Glu Tyr Glu Gly Thr Tyr Thr Ser Arg Asn Arg Gly Tyr
1081 Asp Glu Ala Tyr Gly Asn Asn Pro Ser Val Pro Ala Asp Tyr Ala
1096 Ser Val Tyr Glu Glu Lys Ser Tyr Thr Asp Arg Arg Arg Glu Asn
1111 Pro Cys Glu Ser Asn Arg Gly Tyr Gly Asp Tyr Thr Pro Leu Pro
1126 Ala Gly Tyr Val Thr Lys Glu Leu Glu Tyr Phe Pro Glu Thr Asp
1141 Lys Val Trp Ile Glu Ile Gly Glu Thr Glu Gly Thr Phe Ile Val
1156 Asp Ser Val Glu Leu Leu Leu Met Glu Glu

Fragment 1-*
```

FIGURE 5-5

```
    Met Glu Ile Asn Gln Asn Cys Val Pro Tyr Asn Cys Leu Ser Asn Pro Lys Glu
    ATG GAA ATA AAT CAA AAC TGT GTG CCT TAC AAT TGT TTA AGT AAT CCT AAG GAG
      1           5              10              15              20

Ile Ile Leu Gly Glu Glu Arg Leu Glu Thr Gly Asn Thr Val Ala Asp Ile Ser Leu Gly
    ATA ATA TTA GGC GAG GAA AGG CTA GAA ACA GGG AAT ACT GTA GCA GAC ATT TCA TTA GGG
                 25              30              35              40

Leu Ile Asn Phe Leu Tyr Ser Asn Phe Val Pro Gly Gly Phe Ile Val Gly Leu Leu
    CTT ATT AAT TTT CTA TAT TCT AAT TTT GTA CCA GGA GGA TTT ATA GTA GGT TTA CTA
              45              50              55              60

Glu Leu Ile Trp Gly Phe Ile Gly Pro Ser Gln Trp Asp Ile Phe Leu Ala Gln Ile Glu
    GAA TTA ATA TGG GGA TTT ATA GGG CCT TCG CAA TGG GAT ATT TTT TTA GCT CAA ATT GAG
                 65              70              75              80

Gln Leu Ile Ser Gln Arg Ile Glu Glu Phe Ala Arg Asn Gln Ala Ile Ser Arg Leu Glu
    CAA TTG ATT AGT CAA AGA ATA GAA GAA TTT GCT AGG AAT CAG GCA ATT TCA AGA TTG GAG
                 85              90              95              100
```

FIGURE 6-1

```
Gly Leu Ser Asn  105     110     115         120
                 Leu Tyr Lys Val Tyr Arg Ala Phe Ser Asp Trp Glu Lys Asp Pro
GGG CTA AGC AAT  CTT TAT AAG GTC TAT AGA GCG TTT AGC GAC TGG GAG AAA GAT CCT

Thr Asn Pro Ala  125     130     135         140
                 Leu Arg Glu Glu Met Ile Gln Phe Asn Asp Met Asn Ser Ala Leu
ACT AAT CCT GCT  TTA AGG GAA GAA ATG ATA CAA TTT AAT GAC ATG AAT AGT GCT CTC

Ile Thr Ala Ile  145     150     155         160
                 Pro Leu Phe Arg Val Gln Asn Tyr Glu Val Ala Leu Leu Ser Val Tyr
ATA ACG GCT ATT  CCA CTT TTT AGA GTT CAA AAT TAT GAA GTT GCT CTT TTA TCT GTA TAT

Val Gln Ala Ala  165     170     175         180
                 Asn Leu His Leu Ser Ile Leu Arg Asp Val Ser Val Phe Gly Glu Arg
GTT CAA GCA GCC  AAC TTA CAT TTA TCT ATT TTA AGG GAT GTT TCA GTT TTC GGA GAA AGA

Trp Gly Tyr Asp  185     190     195         200
                 Thr Ala Thr Ile Asn Arg Tyr Ser Asp Leu Thr Ser Leu Ile His
TGG GGA TAT GAT  ACA GCG ACT ATC AAT CGC TAT AGT GAT CTG ACT AGC CTT ATT CAT
```

FIGURE 6-2

```
                            205                         210                      215                         220
Val Tyr Thr Asn His Cys Val Asp Thr Tyr Asn Gln Gly Leu Arg Arg Leu Glu Gly Arg
GTT TAT ACT AAC CAT TGT GTG GAT ACG TAT AAT CAG GGA TTA AGG CGT TTG GAA GGT CGT 225                         230                      235                         240
Phe Leu Ser Asp Trp Ile Val Tyr Asn Arg Phe Arg Arg Gln Leu Thr Ile Ser Val Leu
TTT CTT AGC GAT TGG ATT GTA TAT AAT CGT TTC CGG AGA CAA TTG ACA ATT TCA GTA TTA 245                         250                      255                         260
Asp Ile Val Ala Phe Phe Pro Asn Tyr Asp Ile Arg Thr Tyr Pro Ile Gln Thr Ala Thr
GAT ATT GTT GCG TTT CCA AAT TAT GAT ATT AGA ACA TAT CCA ATT CAA ACA GCT ACT 265                         270                      275                         280
Gln Leu Thr Arg Glu Val Tyr Leu Asp Leu Pro Phe Ile Asn Glu Asn Leu Ser Pro Ala
CAG CTA ACG AGG GAA GTC TAT CTG GAT TTA CCT TTT ATT AAT GAA AAT CTT TCT CCT GCA 285                         290                      295                         300
Ala Ser Tyr Pro Thr Phe Ser Ala Ala Glu Ser Ala Ile Ile Arg Ser Pro His Leu Val
GCA AGC TAT CCA ACC TTT TCA GCT GCT GAA AGT GCT ATA ATT AGA AGT CCT CAT TTA GTA
```

FIGURE 6-3

```
                                                   305                      310                      315                      320
Asp Phe Leu Asn Ser Phe Thr Ile Tyr Thr Asp Ser Leu Ala Arg Tyr Ala Tyr Trp Gly
GAC TTT TTA AAT AGC TTT ACC ATT TAT ACA GAT AGT CTG GCA CGT TAT GCA TGG GGA 325                      330                      335                      340
Gly His Leu Val Asn Ser Phe Arg Thr Gly Thr Thr Asn Leu Ile Arg Ser Pro Leu
GGG CAC TTG GTA AAT TCT TTC CGC ACA GGA ACC ACT AAT TTG ATA AGA TCC CCT TTA 345                      350                      355                      360
Tyr Gly Arg Glu Gly Asn Thr Glu Arg Pro Val Thr Ile Thr Ala Ser Pro Val Pro
TAT GGA AGG GAA GGA AAT ACA GAG CGC CCC GTA ACT ATT ACC GCA TCA CCT GTA CCA 365                      370                      375                      380
Ile Phe Arg Thr Leu Ser Tyr Ile Thr Ile Thr Gly Leu Asp Asn Ser Asn Pro Val Ala Gly Ile
ATA TTT AGA ACA CTT TCA TAT ATT ACA GGC CTT GAC AAT TCA AAT CCT GTA GCT GGA ATC 385                      390                      395                      400
Glu Gly Val Glu Phe Gln Asn Thr Ile Ser Arg Lys Ser Gly Pro Ile
GAG GGA GTG GAA TTC CAA AAT ACT ATA AGT AGA AAA AGC GGT CCA ATA
```

FIGURE 6-4

```
                            405                   410                   415                   420
Asp Phe Ser Glu Leu Pro Pro Gln Asp Ala Ser Val Ser Pro Ala Ile Gly Tyr Ser
GAT TCT AGT GAA TTA CCA CCT CAA GAT GCC AGC GTA TCT CCT GCA ATT GGG TAT AGT 425                   430                   435                   440
His Arg Leu Cys His Ala Thr Phe Leu Glu Arg Ile Ser Gly Pro Arg Ile Ala Gly Thr
CAC CGT TTA TGC CAT GCA ACA TTT TTA GAA CGG ATT AGT GGA CCA AGA ATA GCA GGC ACC 445                   450                   455                   460
Val Phe Ser Trp Thr His Arg Ser Ala Ser Pro Thr Asn Glu Val Ser Pro Ser Arg Ile
GTA TTT TCT TGG ACA CAC CGT AGT GCC CCT ACT AAT GAA GTA AGT CCA TCT AGA ATT 465                   470                   475                   480
Thr Gln Ile Pro Trp Val Lys Ala His Thr Leu Ala Ser Gly Ala Ser Val Ile Lys Gly
ACA CAA ATT CCA TGG GTA AAG GCG CAT ACT CTT GCA TCT GGT GCC TCC GTC ATT AAA GGT 485                   490                   495                   500
Pro Gly Phe Thr Gly Gly Asp Ile Leu Thr Arg Asn Ser Met Gly Glu Leu Gly Thr Leu
CCT GGA TTT ACA GGT GGA GAT ATT CTG ACT AGG AAT AGT ATG GGC GAG CTG GGG ACC TTA
```

FIGURE 6-5

```
                              505                 510                 515                 520
Arg Val Thr Phe Thr Gly Arg Leu Pro Gln Ser Tyr Tyr Ile Arg Phe Arg Tyr Ala Ser
CGA GTA ACC TTC ACA GGA AGA TTA CCA CAA AGT TAT TAT ATA CGT TTC CGT TAT GCT TCG 525                 530                 535                 540
Val Ala Asn Arg Ser Gly Thr Phe Arg Ser Gln Pro Pro Tyr Gly Ile Ser Phe
GTA GCA AAT AGG AGT GGT ACA TTT AGA TCA CAG CCA CCT TAT GGA ATT TCA TTT 545                 550                 555                 560
Pro Lys Thr Met Asp Ala Gly Glu Pro Leu Thr Ser Arg Ser Phe Ala His Thr Thr Leu
CCA AAA ACT ATG GAC GCA GGT GAA CTA ACA TCT CGT TCG TTC CAT ACA ACA CTC 565                 570                 575                 580
Phe Thr Pro Ile Thr Phe Ser Arg Ala Gln Glu Glu Phe Asp Leu Tyr Ile Gln Ser Gly
TTC ACT CCA ATA ACC TTT TCA CGA GCT CAA GAA GAA TTT GAT CTA TAC ATC CAA TCG GGT 585                 590                 595                 600
Val Tyr Ile Asp Arg Ile Glu Phe Ile Pro Val Thr Ala Thr Phe Glu Ala Glu Tyr Asp
GTT TAT ATA GAT CGA ATT GAA TTT ATA CCG GTT ACT GCA ACA TTT GAG GCA GAA TAT GAT
```

FIGURE 6-6

```
                        605                    610                    615                    620
Leu Glu Arg Ala Gln Lys Val Val Asn Ala Leu Phe Thr Ser Asn Gln Leu Gly Leu
TTA GAA AGA GCG CAA AAG GTG GTG AAT GCC CTG ACG TCT AAC CAA CTA GGG CTA 625                    630                    635                    640
Lys Thr Asp Val Thr Asp Tyr His Ile Asp Gln Val Ser Asn Leu Val Ala Cys Leu Ser
AAA ACA GAT GTG ACG GAT TAT CAT ATT GAT CAG GTA TCC AAT CTA GTT GCG TGT TTA TCG 645                    650                    655                    660
Asp Glu Phe Cys Leu Asp Glu Lys Arg Glu Leu Ser Glu Lys Val Lys His Ala Lys Arg
GAT GAA TTT TGT CTG GAT GAA AAG AGA GAA TTG TCC GAG AAA GTT AAA CAT GCA AAG CGA 665                    670                    675                    680
Leu Ser Asp Glu Arg Asn Leu Leu Gln Asp Pro Asn Phe Arg Gly Ile Asn Arg Gln Pro
CTC AGT GAT GAG CGG AAT TTA CTT CAA GAT CCA AAC TTC AGA GGG ATC AAT AGG CAA CCA 685                    690                    695                    700
Asp Arg Gly Trp Arg Gly Ser Thr Asp Ile Thr Ile Gln Gly Gly Asp Asp Val Phe Lys
GAC CGT GGC TGG AGA GGA AGT ACG GAT ATT ACT ATC CAA GGA GGA GAT GAC GTA TTC AAA
```

FIGURE 6-7

```
                                705                710                715                720
Glu Asn Tyr Val Thr Leu Pro Gly Thr Phe Asp Glu Cys Tyr Pro Thr Tyr Leu Tyr Gln
GAG AAT TAC GTT ACG CTA CCG GGT ACC TTT GAT GAG TGC TAT CCA ACG TAT TTA TAT CAA 725                730                735                740
Lys Ile Asp Glu Ser Lys Leu Lys Ala Tyr Thr Arg Tyr Gln Leu Arg Gly Tyr Ile Glu
AAA ATA GAT GAG TCG AAA TTA AAA GCC TAT ACC CGT TAT CAA TTA AGA GGG TAT ATC GAA 745                750                755                760
Asp Ser Gln Asp Leu Glu Ile Tyr Leu Ile Arg Tyr Asn Ala Lys His Glu Ile Val Asn
GAT AGT CAA GAC TTA GAA ATC TAT TTA ATT CGT TAC AAT GCA AAA CAC GAA ATA GTA AAT 765                770                775                780
Val Pro Gly Thr Gly Ser Leu Trp Pro Leu Ser Val Glu Asn Gln Ile Gly Pro Cys Gly
GTA CCA GGT ACA GGA AGT TTA TGG CCT CTT TCT GTA GAA AAT CAA ATT GGA CCT TGT GGA 785                790                795                800
Glu Pro Asn Arg Cys Ala Pro His Leu Glu Trp Asn Pro Asp Leu His Cys Ser Cys Arg
GAA CCG AAT CGA TGC GCG CCA CAC CTT GAA TGG AAT CCT GAT TTA CAC TGT TCC TGC AGA
```

FIGURE 6-8

```
Asp Gly Lys Cys Ala His His Ser His Phe Ser Leu Asp Ile Asp Val Gly Cys
GAC GGG AAA TGT GCA CAT CAT TCT CAT TTC TCT TTG GAC ATT GAT GTT GGA TGT
            805              810             815             820

Thr Asp Leu Asn Glu Gly Leu Asp Val Ile Phe Lys Thr Gln Asp Gly
ACA GAC TTA AAT GAG GGT TTA GAC GTA ATA TTC AAG ACG CAA GAT GGC
            825             830             835             840

His Ala Arg Leu Gly Asn Leu Glu Phe Leu Glu Lys Pro Leu Gly Glu Ala Leu
CAC GCA CGA CTA GGG AAT CTA GAG TTT CTC GAA AAA CCA TTA GGA GAA GCA CTA
            845             850             855             860

Ala Arg Val Lys Arg Ala Glu Lys Trp Arg Asp Lys Arg Glu Thr Leu Gln Leu Glu
GCT CGT GTG AAA AGA GCG GAG AAA TGG AGA GAC AAA CGC GAA ACA TTA CAA TTG GAA
            865             870             875             880

Thr Ile Val Tyr Lys Glu Ala Lys Glu Ser Val Asp Ala Leu Phe Val Asn Ser Gln
ACA ATC GTT TAT AAA GAG GCA AAA GAA TCT GTA GAT GCT TTA TTT GTA AAC TCT CAA
            885             890             895             900
```

FIGURE 6-9

```
                                905              910              915              920
Tyr Asp Arg Leu Gln Ala Asp Thr Asn Ile Ala Met Ile His Ala Asp Lys Arg Val
TAT GAT AGA TTA CAA GCG GAT ACG AAC ATC GCG ATG ATT CAT GCA GAT AAA CGC GTT 925              930              935              940
His Arg Ile Arg Glu Ala Tyr Leu Pro Glu Leu Ser Val Ile Pro Gly Val Asn Ala Ala
CAT AGA ATT CGA GAA GCG TAT CTG CCG GAG CTG TCT GTG ATT CCG GGT GTC AAT GCG GCT 945              950              955              960
Ile Phe Glu Glu Leu Glu Glu Arg Ile Phe Thr Ala Phe Ser Leu Tyr Asp Ala Arg Asn
ATT TTT GAA GAA TTA GAA GAG CGT ATT TTC ACT GCA TTT TCC CTA TAT GAT GCG AGA AAT 965              970              975              980
Ile Lys Asn Gly Asp Phe Asn Asn Gly Leu Leu Cys Trp Asn Val Lys Gly His Val
ATT AAA AAT GGC GAT TTC AAT AAT GGC TTA TTA TGC TGG AAC GTG AAA GGG CAT GTA 985              990              995              1000
Glu Val Glu Glu Gln Asn Asn His Arg Ser Val Leu Val Ile Pro Glu Trp Glu Ala Glu
GAG GTA GAA GAA CAA AAC AAT CAC CGT TCA GTC CTG GTT ATC CCA GAA TGG GAG GCA GAA
```

FIGURE 6-10

```
        1005                  1010                 1015                  1020
Val Ser Gln Glu Val Arg Val Cys Pro Gly Arg Gly Tyr Ile Leu Arg Val Thr Ala Tyr
GTG TCA CAA GAG GTT CGT GTC TGT CCA GGT CGT GGC TAT ATC CTT CGT GTT ACA GCG TAC 1025                  1030                 1035                  1040
Lys Glu Gly Tyr Gly Glu Gly Cys Val Thr Ile His Glu Ile Glu Asn Asn Thr Asp Glu
AAA GAG GGA TAT GGA GAA GGT TGC GTA ACG ATC CAT GAG ATC GAG AAC AAT ACA GAC GAA 1045                  1050                 1055                  1060
Leu Lys Phe Asn Asn Cys Val Glu Glu Val Tyr Pro Asn Asn Thr Val Thr Cys Ile
CTG AAA TTC AAC AAC TGT GTA GAA GAG GTA TAT CCA AAC AAC ACG GTA ACG TGT ATT 1065                  1070                 1075                  1080
Asn Tyr Thr Ala Thr Gln Glu Glu Tyr Glu Gly Thr Tyr Thr Ser Arg Asn Arg Gly Tyr
AAT TAT ACT GCG ACT CAA GAA GAA TAC GAG GGT ACG TAC ACT TCT CGT AAT CGA GGA TAT 1085                  1090                 1095                  1100
Asp Glu Ala Tyr Gly Asn Asn Pro Ser Val Pro Ala Asp Tyr Ala Ser Val Tyr Glu Glu
GAC GAA GCC TAT GGT AAT AAC CCT TCC GTA CCA GCT GAT TAT GCG TCA GTC TAT GAA GAA
```

FIGURE 6-11

```
                    1105                1110                1115                1120
Lys Ser Tyr Thr Asp Arg Arg Arg Glu Asn Pro Cys Glu Ser Asn Arg Gly Tyr Gly Asp
AAA TCG TAT ACA GAT AGA CGA AGA GAG AAT CCT TGT GAA TCT AAC AGA GGA TAT GGA GAT 1125                1130                1135                1140
Tyr Thr Pro Leu Pro Ala Gly Tyr Val Thr Lys Glu Leu Tyr Phe Pro Glu Thr Asp
TAC ACA CCA CTA CCA GCT GGT TAT GTA ACA AAG GAA TTA GAG TAC TTC CCA GAG ACC GAT 1145                1150                1155                1160
Lys Val Trp Ile Glu Ile Gly Glu Thr Gly Thr Phe Ile Val Asp Ser Val Glu Leu
AAG GTA TGG ATT GAG ATT GGA GAA ACA GGA ACA TTC ATC GTG GAC AGC GTG GAA TTA

1165
Leu Leu Met Glu Glu
CTC CTT ATG GAG GAA
```

FIGURE 6-12

|     | 10 | 20 | 30 | 40 | 50 | 60 |
|-----|----|----|----|----|----|----|
| 1   | ATGGAGGAAA | ATAATCAAAA | TCAATGCATA | CCTTACAATT | GTTTAAGTAA | TCCTGAAGAA |
| 61  | GTACTTTTGG | ATGGAGAACG | GATATCAACT | GGTAATTCAT | CAATTGATAT | TTCTCTGTCA |
| 121 | CTTGTTCAGT | TTCTGGTATC | TAACTTTGTA | CCAGGGGGAG | GATTTTTAGT | TGGATTAATA |
| 181 | GATTTGTAT | GGGAATAGT | TGGCCCTTCT | CAATGGGATG | CATTTCTAGT | ACAAATTGAA |
| 241 | CAATTAATTA | ATGAAAGAAT | AGCTGAATTT | GCTAGGAATG | CTGCTATTGC | TAATTTAGAA |

|     | 310 | 320 | 330 | 340 | 350 | 360 |
|-----|-----|-----|-----|-----|-----|-----|
| 301 | GGATTAGGAA | ACAATTTCAA | TATATATGTG | GAAGCATTTA | AAGAATGGGA | AGAAGATCCT |
| 361 | AATAATCCAG | CAACCAGGAC | CAGAGTAATT | GATCGCTTTC | GTATACTTGA | TGGGCTACTT |
| 421 | GAAAGGGACA | TCCCTTCGTT | TCGAATTTCT | GGATTTGAAG | TACCCCTTTT | ATCCGTTTAT |
| 481 | GCTCAAGCGG | CCAATCTGCA | TCTAGCTATA | TTAAGAGATT | CTGTAATTTT | TGGAGAAAGA |
| 541 | TGGGGATTGA | CAACGATAAA | TGTCAATGAA | AACTATAATA | GACTAATTAG | GCATATTGAT |

|     | 610 | 620 | 630 | 640 | 650 | 660 |
|-----|-----|-----|-----|-----|-----|-----|
| 601 | GAATATGCTG | ATCACTGTGC | AAATACGTAT | AATCGGGGAT | TAAATAATTT | ACCGAAATCT |
| 661 | ACGTATCAAG | ATTGGATAAC | ATATAATCGA | TTACGGAGAG | ACTTAACATT | GACTGTATTA |
| 721 | GATATCGCCG | CTTTCTTTCC | AAACTATGAC | AATAGGAGAT | ATCCAATTCA | GCCAGTTGGT |
| 781 | CAACTAACAA | GGGAAGTTTA | TACGGACCCA | TTAATTAATT | TTAATCCACA | GTTACAGTCT |
| 841 | GTAGCTCAAT | TACCTACTTT | TAACGTTATG | GAGAGCAGCG | CAATTAGAAA | TCCTCATTTA |

FIGURE 7-1

|      | 910 | 920 | 930 | 940 | 950 | 960 |
|------|-----|-----|-----|-----|-----|-----|
| 901  | TTTGATATAT | TGAATAATCT | TACAATCTTT | ACGGATTGGT | TTAGTGTTGG | ACGCAATTTT |
| 961  | TATTGGGAG  | GACATCGAGT | AATATCTAGC | CTTATAGGAG | GTGGTAACAT | AACATCTCCT |
| 1021 | ATATATGGAA | GAGAGGCGAA | CCAGGAGCCT | CCAAGATCCT | TTACTTTTAA | TGGACCGGTA |
| 1081 | TTTAGGACTT | TATCAAATCC | TACTTTACGA | AACCTGGCC  | AGCGCCACCA |            |
| 1141 | TTTAATTTAC | GTGGTGTTGA | AGGAGTAGAA | CTACAAATAG | TTTTCTACAC | CTTTACGTAT |
|      | 1210 | 1220 | 1230 | 1240 | 1250 | 1260 |
| 1201 | CGAGGAAGAG | GTACGGTTGA | TTCTTTAACT | GAATTACCGC | CTGAGGATAA | TAGTGTGCCA |
| 1261 | CCTCGCGAAG | GATATAGTCA | TCGTTTATGT | CATGCAACTT | TGTTCAAAG  | ATCTGGAACA |
| 1321 | CCTTTTTAA  | CAACTGGTGT | AGTATTTCT  | TGGACGCATC | GTAGTGCAAC | TCTTACAAAT |
| 1381 | ACAATTGATC | CAGAGAGAAT | TAATCAAATA | CCTTTAGTGA | AAGGATTAG  | AGTTTGGGGG |
| 1441 | GGCACCCTG  | TCATTACAGG | ACCAGGATT  | ACAGGAGGGG | ATATCCTTCG | AAGAAATACC |
|      | 1510 | 1520 | 1530 | 1540 | 1550 | 1560 |
| 1501 | TTTGGTGATT | TTGTATCTCT | ACAAGTCAAT | ATTAATTCAC | CAATTACCCA | AAGATACCGT |
| 1561 | TTAAGATTC  | GTTACGCTTC | CAGTAGGGAT | GCACGAGTTA | TAGTATTAAC | AGGAGCGGCA |
| 1621 | TCCACAGGAG | TGGGAGGCCA | AGTTAGTGTA | AATATGCCTC | TTCAGAAAAC | TATGAAATA  |
| 1681 | GGGAGAACT  | TAACATCTAG | AACATTAGA  | TATACCGATT | TTAGTAATCC | TTTTCATTT  |
| 1741 | AGAGCTAATC | CAGATATAAT | TGGGATAAGT | GAACAACCTC | TATTGGTGC  | AGGTTCTATT |

FIGURE 7-2

```
                              1810                 1820                 1830                 1840                 1850                 1860
1801  AGTAGCGGTG  AACTTTATAT  AGATAAAATT  GAAATTATTC  TAGCAGATGC  AACATTTGAA
1861  GCAGAATCTG  ATTTAGAAAG  AGCACAAAAG  GCGGTGAATG  CCCTGTTTAC  TTCTTCCAAT
1921  CAAATCGGGT  TAAAAACCGA  TGTGACGGAT  TATCATATTG  ATCAAGTATC  CAATTAGTTG
1981  GATTGTTTAT  CAGATGAATT  TTGTCTGGAT  GAAAAGCGAG  AATTGTCCGA  GAAAGTCAAA
2041  CATGCGAAGC  GACTCAGTGA  TGAGCGGAAT  TTACTTCAAG  ATCCAAACTT  CAGAGGGATC 2110                 2120                 2130                 2140                 2150                 2160
2101  AATAGACAAC  CAGACCGTGG  CTGGAGAGGA  AGTACAGATA  TTACCATCCA  AGGAGGAGAT
2161  GACGTATTCA  AAGAGAATTA  CGTCACACTA  CCGGGTACCG  TTGATGAGTG  CTATCCAACG
2221  TATTTATATC  AGAAAATAGA  TGAGTCGAAA  TTAAAAGCTT  ATACCCGTTA  TGAATTAAGA
2281  GGGTATATCG  AAGATAGTCA  AGACTTAGAA  ATCTATTTGA  TCCGTTACAA  TGCAAAACAC
2341  GAAATAGTAA  ATGTGCCAGG  CACGGGTCC  TTATGGCCGC  TTTCAGCCCA  AGTCCAATC 2410                 2420                 2430                 2440                 2450                 2460
2401  GGAAAGTGTG  GAGAACCGAA  TCGATGCGCG  CCACACCTTG  AATGGAATCC  TGATCTAGAT
2461  TGTTCCTGCA  GAGACGGGGA  AAAATGTGCA  CATCATTCCC  ATCATTTCAC  CTTGGATATT
2521  GATGTTGGAT  GTACAGACTT  AAATGAGGAC  TTAGGTGTAT  GGGTGATATT  CAAGATTAAG
2581  ACGCAAGATG  GCCATGCAAG  ACTAGGGAAT  CTAGAGTTTC  TCGAAGAGAA  ACCATTATTA
2641  GGGGAAGCAC  TAGCTCGTGT  GAAAAGAGCG  GAGAAGAAGT  GGAGAGACAA  ACGAGAGAAA
```

FIGURE 7-3

```
2710       2720       2730       2740       2750       2760
2701 CTGCAGTTGG AAACAAATAT TGTTTATAAA GAGGCAAAAG AATCTGTAGA TGCTTTATTT
2761 GTAAACTCTC AATATGATAG ATTACAAGTG GATACGAACA TCGCAATGAT TCATGCGGCA
2821 GATAAACGCG TTCATAGAAT CCGGGAAGCG TATCTGCCAG AGTTGTCTGT GATTCCAGGT
2881 GTCAATGCGG CCATTTTCGA AGAATTAGAG GGACGTATTT TTACAGCGTA TTCCTTATAT
2941 GATGCGAGAA ATGTCATTAA AAATGGCGAT TTCAATAATG GCTTATTATG CTGGAACGTG
         3010       3020       3030       3040       3050       3060
3001 AAAGGTCATG TAGATGTAGA AGAGCAAAAC AACCACCGTT CGGTCCTTGT TATCCCAGAA
3061 TGGGAGGCAG AAGTGTCACA AGAGGTTCGT GTCTGTCCAG GTCGTGGCTA TATCCTTCGT
3121 GTCACAGCAT ATAAAGAGGG GGCTGCGTAA CGATCCATGA CGATCGAAGAC
3181 AATACAGACG AACTGAAATT CAGCAACTGT GTAGAAGAGG AAGTATATCC AAACAACACA
3241 GTAACGTGTA ATAATTATAC TGGGACTCAA GAAGAATATG AGGGTACGTA CACTTCTCGT
         3310       3320       3330       3340       3350       3360
3301 AATCAAGGAT ATGACGAAGC CTATGGTAAT AACCCTTCCG TACCAGCTGA TTACGCTTCA
3361 GTCTATGAAG AAAAATCGTA TACAGATGGA CGAAGAGAGA ATCCTTGTGA ATCTAACAGA
3421 GGCTATGGGG ATTACACACC ACTACCGGCT GGTTATGTAA CAAAGGATTT AGAGTACTTC
3481 CCAGAGACCG ATAAGGTATG GATTGAGATC GGAGAAACAG AAGGAACATT CATCGTGGAT
3541 AGCGTGGAAT TACTCCTTAT GGAGGAA

Segment 1-*
```

FIGURE 7-4

|     |     |     |     |     | 5   |     |     |     |     | 10  |     |     |     |     | 15  |
| --- | --- | --- | --- | --- | --- | --- | --- | --- | --- | --- | --- | --- | --- | --- | --- |
| 1   | Met | Glu | Asn | Asn | Gln | Cys | Ile | Pro | Tyr | Asn | Cys | Leu |
| 16  | Ser | Asn | Pro | Glu | Val | Leu | Asp | Gly | Glu | Arg | Ile | Ser | Thr |
| 31  | Gly | Asn | Ser | Ser | Ile | Asp | Leu | Ser | Leu | Val | Gln | Phe | Leu |
| 46  | Val | Ser | Asn | Phe | Val | Pro | Gly | Gly | Phe | Leu | Val | Gly | Leu | Ile |
| 61  | Asp | Phe | Val | Trp | Gly | Ile | Val | Gly | Pro | Ser | Gln | Trp | Asp | Ala | Phe |
| 76  | Leu | Val | Gln | Ile | Glu | Gln | Leu | Ile | Asn | Glu | Arg | Ile | Ala | Glu | Phe |
| 91  | Ala | Arg | Asn | Ala | Ala | Ile | Ala | Asn | Leu | Gly | Gly | Leu | Gly | Asn | Asn |
| 106 | Phe | Asn | Ile | Tyr | Val | Glu | Ala | Phe | Lys | Glu | Trp | Glu | Glu | Asp | Pro |
| 121 | Asn | Asn | Pro | Ala | Thr | Arg | Thr | Arg | Val | Ile | Asp | Arg | Phe | Arg | Ile |
| 136 | Leu | Asp | Gly | Leu | Leu | Glu | Arg | Asp | Ile | Pro | Ser | Phe | Arg | Ile | Ser |
| 151 | Gly | Phe | Glu | Val | Pro | Leu | Leu | Ser | Val | Tyr | Ala | Gln | Ala | Ala | Asn |
| 166 | Leu | His | Leu | Ala | Ile | Leu | Arg | Asp | Ser | Val | Ile | Phe | Gly | Glu | Arg |
| 181 | Trp | Gly | Leu | Thr | Thr | Ile | Asn | Val | Asn | Glu | Asn | Tyr | Asn | Arg | Leu |
| 196 | Ile | Arg | His | Ile | Asp | Glu | Tyr | Ala | Asp | His | Cys | Ala | Asn | Thr | Tyr |
| 211 | Asn | Arg | Gly | Leu | Asn | Asn | Leu | Pro | Lys | Ser | Thr | Tyr | Gln | Asp | Trp |

FIGURE 8-1

| | | | | | | | | | | | | | | | |
|---|---|---|---|---|---|---|---|---|---|---|---|---|---|---|---|
| 226 | Ile | Thr | Tyr | Asn | Arg | Leu | Arg | Arg | Asp | Leu | Thr | Leu | Thr | Val | Leu |
| 241 | Asp | Ile | Ala | Ala | Phe | Pro | Asn | Tyr | Asp | Asn | Arg | Arg | Tyr | Pro |
| 256 | Ile | Gln | Pro | Val | Gly | Gln | Leu | Thr | Arg | Glu | Val | Tyr | Thr | Asp | Pro |
| 271 | Leu | Ile | Asn | Phe | Asn | Pro | Gln | Leu | Ser | Val | Ala | Gln | Leu | Pro |
| 286 | Thr | Phe | Asn | Val | Met | Glu | Ser | Ser | Ala | Ile | Arg | Asn | Pro | His | Leu |
| 301 | Phe | Asp | Ile | Leu | Asn | Leu | Thr | Ile | Phe | Thr | Asp | Trp | Phe | Ser |
| 316 | Val | Gly | Arg | Asn | Phe | Tyr | Trp | Gly | His | Arg | Val | Ile | Ser | Ser |
| 331 | Leu | Ile | Gly | Gly | Gly | Asn | Ile | Thr | Ser | Pro | Ile | Tyr | Gly | Arg | Glu |
| 346 | Ala | Asn | Gln | Glu | Pro | Pro | Arg | Ser | Phe | Thr | Phe | Asn | Gly | Pro | Val |
| 361 | Phe | Arg | Thr | Leu | Ser | Asn | Pro | Thr | Leu | Arg | Leu | Leu | Gln | Gln | Pro |
| 376 | Trp | Pro | Ala | Pro | Pro | Phe | Asn | Leu | Arg | Gly | Val | Glu | Gly | Val | Glu |
| 391 | Phe | Ser | Thr | Pro | Thr | Asn | Ser | Phe | Thr | Tyr | Arg | Gly | Arg | Gly | Thr |
| 406 | Val | Asp | Ser | Leu | Thr | Glu | Leu | Pro | Pro | Glu | Asp | Asn | Ser | Val | Pro |
| 421 | Pro | Arg | Glu | Gly | Tyr | Ser | His | Arg | Leu | Cys | His | Ala | Thr | Phe | Val |
| 436 | Gln | Arg | Ser | Gly | Thr | Pro | Phe | Leu | Thr | Thr | Gly | Val | Val | Phe | Ser |

FIGURE 8-2

| | | | | | | | | | |
|---|---|---|---|---|---|---|---|---|---|
| 451 | Trp | Thr | His | Arg | Ser | Ala | Thr | Leu | Thr | Asn | Thr | Ile | Asp | Pro | Glu |
| 466 | Arg | Ile | Asn | Gln | Ile | Pro | Leu | Val | Lys | Gly | Phe | Arg | Val | Trp | Gly |
| 481 | Gly | Thr | Ser | Val | Ile | Thr | Gly | Pro | Gly | Phe | Thr | Gly | Gly | Asp | Ile |
| 496 | Leu | Arg | Arg | Asn | Thr | Phe | Gly | Asp | Phe | Val | Ser | Leu | Gln | Val | Asn |
| 511 | Ile | Asn | Ser | Pro | Ile | Thr | Gln | Arg | Tyr | Arg | Leu | Arg | Phe | Arg | Tyr |
| 526 | Ala | Ser | Ser | Arg | Asp | Ala | Arg | Val | Ile | Val | Leu | Thr | Gly | Ala | Ala |
| 541 | Ser | Thr | Gly | Val | Gly | Gly | Gln | Val | Ser | Val | Asn | Met | Pro | Leu | Gln |
| 556 | Lys | Thr | Met | Glu | Ile | Gly | Glu | Asn | Leu | Thr | Ser | Arg | Thr | Phe | Arg |
| 571 | Tyr | Thr | Asp | Phe | Ser | Asn | Pro | Phe | Ser | Phe | Arg | Ala | Asn | Pro | Asp |
| 586 | Ile | Ile | Gly | Ile | Ser | Glu | Gln | Pro | Leu | Phe | Gly | Ala | Gly | Ser | Ile |
| 601 | Ser | Ser | Gly | Glu | Leu | Tyr | Ile | Asp | Lys | Ile | Glu | Ile | Ile | Leu | Ala |
| 616 | Asp | Ala | Thr | Phe | Glu | Ala | Glu | Ser | Asp | Leu | Glu | Arg | Ala | Gln | Lys |
| 631 | Ala | Val | Asn | Ala | Leu | Phe | Thr | Ser | Ser | Asn | Gln | Ile | Gly | Leu | Lys |
| 646 | Thr | Asp | Val | Thr | Asp | Tyr | His | Ile | Asp | Gln | Val | Ser | Asn | Leu | Val |
| 661 | Asp | Cys | Leu | Ser | Asp | Glu | Phe | Cys | Leu | Asp | Glu | Lys | Arg | Glu | Leu |

FIGURE 8-3

```
676 Ser Glu Lys Val Lys His Ala Lys Arg Leu Ser Asp Glu Arg Asn
691 Leu Leu Gln Asp Pro Asn Phe Arg Gly Ile Asn Arg Gln Pro Asp
706 Arg Gly Trp Arg Gly Ser Thr Asp Ile Thr Ile Gln Gly Gly Asp
721 Asp Val Phe Lys Glu Asn Tyr Val Thr Leu Pro Gly Thr Val Asp
736 Glu Cys Tyr Pro Thr Leu Tyr Leu Gln Ile Ile Asp Glu Ser Lys
751 Leu Lys Ala Tyr Arg Arg Tyr Glu Tyr Lys Arg Gly Tyr Ile Asp
766 Ser Gln Asp Leu Glu Ile Ile Tyr Leu Ile Leu Arg Tyr Asn Ala Lys His
781 Glu Ile Val Asn Val Pro Gly Thr Gly Ser Leu Trp Pro Leu Ser
796 Ala Gln Ser Pro Ile Gly Lys Cys Gly Glu Pro Asn Arg Cys Ala
811 Pro His Leu Glu Trp Asn Pro Asp Leu Asp Cys Ser Cys Arg Asp
826 Gly Glu Lys Cys Ala His His Ser His Phe Thr Leu Asp Ile
841 Asp Val Gly Cys Thr Asp Leu Asn Glu Asp Leu Gly Val Trp Val
856 Ile Phe Lys Ile Lys Thr Gln Asp Gly His Ala Arg Leu Gly Asn
871 Leu Glu Phe Leu Glu Glu Lys Pro Leu Leu Gly Glu Ala Leu Ala
886 Arg Val Lys Arg Ala Gly Lys Lys Trp Arg Asp Lys Arg Glu Lys
```

FIGURE 8-4

```
 901 Leu Gln Leu Glu Thr Asn Ile Val Tyr Lys Glu Ala Lys Glu Ser
 916 Val Asp Ala Leu Phe Val Asn Ser Gln Tyr Asp Arg Leu Gln Val
 931 Asp Thr Asn Ile Ala Met Ile His Ala Ala Asp Lys Arg Val His
 946 Arg Ile Arg Glu Ala Tyr Leu Pro Glu Leu Ser Val Ile Pro Gly
 961 Val Asn Ala Ala Ile Phe Glu Leu Glu Gly Arg Ile Phe Thr
 976 Ala Tyr Ser Leu Tyr Asp Ala Arg Asn Val Ile Lys Asn Gly Asp
 991 Phe Asn Gly Leu Leu Cys Trp Asn Val Lys Gly His Val Asp
1006 Val Glu Gln Asn Asn His Arg Ser Val Leu Val Ile Pro Glu
1021 Trp Glu Ala Glu Val Ser Gln Glu Val Arg Val Cys Pro Gly Arg
1036 Gly Tyr Ile Leu Arg Val Thr Ala Tyr Lys Glu Gly Tyr Gly Glu
1051 Gly Cys Val Thr Ile His Glu Ile Glu Asp Asn Thr Asp Glu Leu
1066 Lys Phe Ser Asn Cys Val Glu Glu Val Val Tyr Pro Asn Asn Thr
1081 Val Thr Tyr Asn Tyr Thr Gly Thr Gln Glu Gln Glu Tyr Glu Gly
1096 Thr Tyr Ser Arg Asn Gln Gly Tyr Asp Tyr Ala Ser Gly Asn
1111 Asn Pro Ser Val Pro Ala Asp Tyr Ala Ser Val Tyr Glu Glu Lys
1126 Ser Tyr Thr Asp Gly Arg Arg Glu Asn Pro Cys Glu Ser Asn Arg
1141 Gly Tyr Gly Asp Tyr Thr Pro Leu Pro Ala Gly Tyr Val Thr Lys
1156 Asp Leu Glu Tyr Phe Pro Glu Thr Asp Lys Val Trp Ile Glu Ile
1171 Gly Glu Thr Gly Gly Thr Phe Ile Val Asp Ser Val Glu Leu Leu
1186 Leu Met Glu Glu
```

Fragment 1-*

FIGURE 8-5

```
                                       5                        10                       15                    20
Met Glu Asn Asn Gln Cys Ile Pro Tyr Asn Cys Leu Ser Asn Pro Glu Glu
ATG GAG AAT AAT CAA TGC ATA CCT TAC AAT TGT TTA AGT AAT CCT GAA GAA 25                       30                       35                    40
Val Leu Leu Asp Gly Glu Arg Ile Ser Thr Gly Asn Ser Ser Ile Asp Ile Ser Leu Ser
GTA CTT TTG GAT GGA GAA CGG ATA TCA ACT GGT AAT TCA TCA ATT GAT ATT TCT CTG TCA 45                       50                       55                    60
Leu Val Gln Phe Leu Val Ser Asn Phe Val Pro Gly Gly Gly Phe Leu Val Gly Leu Ile
CTT GTT CAG TTT CTG GTA TCT AAC TTT GTA CCA GGG GGA TTT TTA GTT GGA TTA ATA 65                       70                       75                    80
Asp Phe Val Trp Gly Ile Val Gly Pro Ser Gln Trp Asp Ala Phe Leu Val Gln Ile Glu
GAT TTT GTA TGG GGA ATA GTT GGC CCT TCT CAA TGG GAT GCA TTT CTA GTA CAA ATT GAA
```

FIGURE 9-1

|    |     |     |     | 85  |     |     |     |     | 90  |     |     |     |     | 95  |     |     |     |     | 100 |
|----|-----|-----|-----|-----|-----|-----|-----|-----|-----|-----|-----|-----|-----|-----|-----|-----|-----|-----|-----|
| Gln | Leu | Ile | Asn | Glu | Arg | Ile | Ala | Glu | Phe | Ala | Arg | Asn | Ala | Ala | Ile | Ala | Asn | Leu | Glu |
| CAA | TTA | ATT | AAT | GAA | AGA | ATA | GCT | GAA | TTT | GCT | AGG | AAT | GCT | GCT | ATT | GCT | AAT | TTA | GAA |

|    |     |     |     | 105 |     |     |     |     | 110 |     |     |     |     | 115 |     |     |     |     | 120 |
|----|-----|-----|-----|-----|-----|-----|-----|-----|-----|-----|-----|-----|-----|-----|-----|-----|-----|-----|-----|
| Gly | Leu | Gly | Asn | Asn | Phe | Asn | Ile | Tyr | Val | Glu | Ala | Phe | Lys | Glu | Trp | Glu | Glu | Asp | Pro |
| GGA | TTA | GGA | AAC | AAT | TTC | AAT | ATA | TAT | GTG | GAA | GCA | TTT | AAA | GAA | TGG | GAA | GAA | GAT | CCT |

|    |     |     |     | 125 |     |     |     |     | 130 |     |     |     |     | 135 |     |     |     |     | 140 |
|----|-----|-----|-----|-----|-----|-----|-----|-----|-----|-----|-----|-----|-----|-----|-----|-----|-----|-----|-----|
| Asn | Asn | Pro | Ala | Thr | Arg | Thr | Arg | Val | Ile | Asp | Arg | Phe | Arg | Ile | Leu | Asp | Gly | Leu | Leu |
| AAT | AAT | CCA | GCA | ACC | AGG | ACC | AGA | GTA | ATT | GAT | CGC | TTT | CGT | ATA | CTT | GAT | GGG | CTA | CTT |

|    |     |     |     | 145 |     |     |     |     | 150 |     |     |     |     | 155 |     |     |     |     | 160 |
|----|-----|-----|-----|-----|-----|-----|-----|-----|-----|-----|-----|-----|-----|-----|-----|-----|-----|-----|-----|
| Glu | Arg | Asp | Ile | Pro | Ser | Phe | Arg | Ile | Ser | Gly | Phe | Glu | Val | Pro | Leu | Leu | Ser | Val | Tyr |
| GAA | AGG | GAC | ATT | CCT | TCG | TTT | CGA | ATT | TCT | GGA | TTT | GAA | GTA | CCC | CTT | TTA | TCC | GTT | TAT |

|    |     |     |     | 165 |     |     |     |     | 170 |     |     |     |     | 175 |     |     |     |     | 180 |
|----|-----|-----|-----|-----|-----|-----|-----|-----|-----|-----|-----|-----|-----|-----|-----|-----|-----|-----|-----|
| Ala | Gln | Ala | Ala | Asn | Leu | His | Leu | Ala | Ile | Leu | Arg | Asp | Ser | Val | Ile | Phe | Gly | Glu | Arg |
| GCT | CAA | GCG | GCC | AAT | CTG | CAT | CTA | GCT | ATA | TTA | AGA | GAT | TCT | GTA | ATT | TTT | GGA | GAA | AGA |

FIGURE 9-2

```
                                            185                   190                   195                   200
Trp Gly Leu Thr Thr Ile Asn Val Asn Glu Asn Tyr Asn Arg Leu Ile Arg His Ile Asp
TGG GGA TTG ACA ACG ATA AAT GTC AAT GAA AAC TAT AAT AGA CTA ATT AGG CAT ATT GAT 205                   210                   215                   220
Glu Tyr Ala Asp His Cys Ala Asn Thr Tyr Asn Arg Gly Leu Asn Leu Pro Lys Ser
GAA TAT GCT GAT CAC TGT GCA AAT ACG TAT AAT CGG GGA TTA AAT TTA CCG AAA TCT 225                   230                   235                   240
Thr Tyr Gln Asp Trp Ile Thr Tyr Asn Arg Leu Arg Arg Asp Leu Thr Leu Thr Val Leu
ACG TAT CAA GAT TGG ATA ACA TAT AAT CGA TTA CGG AGA GAC TTA ACA TTG ACT GTA TTA 245                   250                   255                   260
Asp Ile Ala Ala Phe Phe Pro Asn Tyr Asp Asn Arg Arg Tyr Pro Ile Gln Pro Val Gly
GAT ATC GCA GCT TTC TTT CCA AAC TAT GAC AAT AGG AGA TAT CCA ATT CAG CCA GTT GGT 265                   270                   275                   280
Gln Leu Thr Arg Glu Val Tyr Thr Asp Pro Leu Ile Asn Phe Asn Pro Gln Leu Gln Ser
CAA CTA ACA AGG GAA GTT TAT ACG GAC CCA CTA ATT AAT TTT AAT CCA CAG TTA CAG TCT
```

FIGURE 9-3

|  |  | 285 |  |  | 290 |  |  | 295 |  |  | 300 |
|---|---|---|---|---|---|---|---|---|---|---|---|
| Val | Ala | Gln | Leu | Pro | Thr | Phe | Asn | Val | Met | Glu | Ser | Ser | Ala | Ile | Arg | Asn | Pro | His | Leu |
| GTA | GCT | CAA | TTA | CCT | ACT | TTT | AAC | GTT | ATG | GAG | AGC | AGC | GCA | ATT | AGA | AAT | CCT | CAT | TTA |

|  |  | 305 |  |  | 310 |  |  | 315 |  |  | 320 |
| Phe | Asp | Ile | Leu | Asn | Asn | Leu | Thr | Ile | Phe | Thr | Asp | Trp | Phe | Ser | Val | Gly | Arg | Asn | Phe |
| TTT | GAT | ATA | TTG | AAT | AAT | CTT | ACA | ATC | TTT | ACG | GAT | TGG | TTT | AGT | GTT | GGA | CGC | AAT | TTT |

|  |  | 325 |  |  | 330 |  |  | 335 |  |  | 340 |
| Tyr | Trp | Gly | Gly | His | Arg | Val | Ile | Ser | Leu | Ile | Gly | Gly | Asn | Ile | Thr | Ser | Pro |
| TAT | TGG | GGA | GGA | CAT | CGA | GTA | ATA | TCT | CTT | ATA | GGA | GGT | AAC | ATA | ACA | TCT | CCT |

|  |  | 345 |  |  | 350 |  |  | 355 |  |  | 360 |
| Ile | Tyr | Gly | Arg | Glu | Ala | Asn | Gln | Glu | Pro | Pro | Arg | Ser | Phe | Thr | Phe | Asn | Gly | Pro | Val |
| ATA | TAT | GGA | AGA | GAG | GCG | AAC | CAG | GAG | CCT | CCA | AGA | TCC | TTT | ACT | TTT | AAT | GGA | CCG | GTA |

|  |  | 365 |  |  | 370 |  |  | 375 |  |  | 380 |
| Phe | Arg | Thr | Leu | Ser | Asn | Pro | Thr | Leu | Arg | Leu | Leu | Gln | Gln | Pro | Trp | Pro | Ala | Pro | Pro |
| TTT | AGG | ACT | TTA | TCA | AAT | CCT | ACT | TTA | CGA | TTA | TTA | CAG | CAA | CCT | TGG | CCA | GCG | CCA | CCA |

FIGURE 9-4

```
                  385         390         395         400
Phe Asn Leu Arg Gly Val Glu Gly Val Phe Ser Thr Pro Asn Ser Phe Thr Tyr
TTT AAT TTA CGT GGT GTT GAA GGA GTA TTT TCT ACA CCT AAT AGC TTT ACG TAT 405         410         415         420
Arg Gly Arg Gly Thr Val Asp Ser Leu Thr Glu Leu Pro Pro Glu Asp Asn Ser Val Pro
CGA GGA AGA GGT ACG GTT GAT TCT TTA ACT GAA TTA CCG CCT GAG GAT AAT AGT GTG CCA 425         430         435         440
Pro Arg Glu Gly Tyr Ser His Arg Leu Cys His Ala Thr Phe Val Gln Arg Ser Gly Thr
CCT CGC GAA GGA TAT AGT CAT CGT TTA TGT CAT GCA ACT TTT CAA AGA TCT GGA ACA 445         450         455         460
Pro Phe Leu Thr Thr Gly Val Val Phe Ser Trp Thr His Arg Ser Ala Thr Leu Thr Asn
CCT TTT TTA ACA GGT GTA TTT TCT TGG ACG CAT CGT AGT GCA ACT CTT ACA AAT 465         470         475         480
Thr Ile Asp Pro Glu Arg Ile Asn Gln Ile Pro Leu Val Lys Gly Phe Arg Val Trp Gly
ACA ATT GAT CCA GAG AGA ATT AAT CAA ATA CCT TTA GTG AAA GGA TTT AGA GTT TGG GGG
```

FIGURE 9-5

```
                485           490           495           500
Gly Thr Ser Val Ile Thr Gly Pro Gly Phe Thr Gly Gly Asp Ile Leu Arg Arg Asn Thr
GGC ACC TCT GTC ATT ACA GGA CCA GGA TTT ACA GGA GGG GAT ATC CTT CGA AGA AAT ACC
                505           510           515           520
Phe Gly Asp Phe Val Ser Leu Gln Val Asn Ile Asn Ser Pro Ile Thr Gln Arg Tyr Arg
TTT GGT GAT TTT GTA TCT CTA CAA GTC AAT ATT AAT TCA CCA ATT ACC CAA AGA TAC CGT
                525           530           535           540
Leu Arg Phe Arg Tyr Ala Ser Ser Arg Asp Ala Arg Val Ile Val Leu Thr Gly Ala Ala
TTA AGA TTT CGT TAC GCT TCC AGT AGG GAT GCA CGA GTT ATA GTA TTA ACA GGA GCG GCA
                545           550           555           560
Ser Thr Gly Val Gly Gly Gln Val Ser Val Asn Met Pro Leu Gln Lys Thr Met Glu Ile
TCC ACA GGA GTG GGA GGC CAA GTT AGT AAT ATG CCT CTT CAG AAA ACT ATG GAA ATA
                565           570           575           580
Gly Glu Asn Leu Thr Ser Arg Thr Phe Arg Tyr Thr Asp Phe Ser Asn Pro Phe Ser Phe
GGG GAG AAC TTA ACA TCT AGA ACA TTT AGA TAT ACC GAT TTT AGT AAT CCT TTT TCA TTT
```

FIGURE 9-6

```
                          585              590              595          600
Arg Ala Asn Pro Asp Ile Ile Gly Ser Glu Gln Pro Leu Phe Gly Ala Gly Ser Ile
AGA GCT AAT CCA GAT ATA ATT GGG AGT GAA CAA CCT CTA TTT GGT GCA GGT TCT ATT 605              610              615          620
Ser Ser Gly Glu Leu Tyr Ile Asp Lys Ile Glu Ile Ile Leu Ala Asp Ala Thr Phe Glu
AGT AGC GGT GAA CTT TAT ATA GAT AAA ATT GAA ATT CTA GCA GAT GCA ACA TTT GAA 625              630              635          640
Ala Glu Ser Asp Leu Glu Arg Ala Gln Lys Ala Val Asn Ala Leu Phe Thr Ser Ser Asn
GCA GAA TCT GAT TTA GAA AGA GCA CAA AAG GCG GTG AAT GCC CTG TTT ACT TCT TCC AAT 645              650              655          660
Gln Ile Gly Leu Lys Thr Asp Val Thr Asp Tyr His Ile Asp Gln Val Ser Asn Leu Val
CAA ATC GGG TTA AAA ACC GAT GTG ACG GAT TAT CAT ATT GAT CAA GTA TCC AAT TTA GTG 665              670              675          680
Asp Cys Leu Ser Asp Glu Phe Cys Leu Asp Glu Lys Arg Glu Leu Ser Glu Lys Val Lys
GAT TGT TTA TCA GAT GAA TTT TGT CTG GAT GAA AAG CGA GAA TTG TCC GAG AAA GTC AAA
```

FIGURE 9-7

|     |     |     | 685 |     |     |     |     | 690 |     |     |     |     | 695 |     |     |     |     | 700 |
| --- | --- | --- | --- | --- | --- | --- | --- | --- | --- | --- | --- | --- | --- | --- | --- | --- | --- | --- |
| His | Ala | Lys | Arg | Leu | Ser | Asp | Glu | Arg | Asn | Leu | Leu | Gln | Asp | Pro | Asn | Phe | Arg | Gly | Ile |
| CAT | GCG | AAG | CGA | CTC | AGT | GAT | GAG | CGG | AAT | TTA | CTT | CAA | GAT | CCA | AAC | TTC | AGA | GGG | ATC |

|     |     |     | 705 |     |     |     |     | 710 |     |     |     |     | 715 |     |     |     |     | 720 |
| --- | --- | --- | --- | --- | --- | --- | --- | --- | --- | --- | --- | --- | --- | --- | --- | --- | --- | --- |
| Asn | Arg | Gln | Pro | Asp | Arg | Gly | Trp | Arg | Gly | Ser | Thr | Asp | Ile | Thr | Ile | Gln | Gly | Gly | Asp |
| AAT | AGA | CAA | CCA | GAC | CGT | GGC | TGG | AGA | GGA | AGT | ACA | GAT | ATT | ACC | ATC | CAA | GGA | GGA | GAT |

|     |     |     | 725 |     |     |     |     | 730 |     |     |     |     | 735 |     |     |     |     | 740 |
| --- | --- | --- | --- | --- | --- | --- | --- | --- | --- | --- | --- | --- | --- | --- | --- | --- | --- | --- |
| Asp | Val | Phe | Lys | Glu | Asn | Tyr | Val | Thr | Leu | Pro | Gly | Thr | Val | Asp | Glu | Cys | Tyr | Pro | Thr |
| GAC | GTA | TTC | AAA | GAG | AAT | TAC | GTC | ACA | CTA | CCG | GGT | ACC | GTT | GAT | GAG | TGC | TAT | CCA | ACG |

|     |     |     | 745 |     |     |     |     | 750 |     |     |     |     | 755 |     |     |     |     | 760 |
| --- | --- | --- | --- | --- | --- | --- | --- | --- | --- | --- | --- | --- | --- | --- | --- | --- | --- | --- |
| Tyr | Leu | Gln | Lys | Ile | Asp | Glu | Ser | Lys | Leu | Lys | Ala | Tyr | Thr | Arg | Tyr | Glu | Leu | Arg |
| TAT | TTA | CAG | AAA | ATA | GAT | GAG | TCG | AAA | TTA | AAA | GCT | TAT | ACC | CGT | TAT | GAA | TTA | AGA |

|     |     |     | 765 |     |     |     |     | 770 |     |     |     |     | 775 |     |     |     |     | 780 |
| --- | --- | --- | --- | --- | --- | --- | --- | --- | --- | --- | --- | --- | --- | --- | --- | --- | --- | --- |
| Gly | Tyr | Ile | Glu | Asp | Ser | Gln | Asp | Leu | Glu | Ile | Tyr | Leu | Ile | Arg | Tyr | Asn | Ala | Lys | His |
| GGG | TAT | ATC | GAA | GAT | AGT | CAA | GAC | TTA | GAA | ATC | TAT | TTG | ATC | CGT | TAC | AAT | GCA | AAA | CAC |

FIGURE 9-8

```
                        785 Val Pro Gly Thr Gly Ser Leu Trp Pro Leu Ser Ala Gln Ser Pro Ile 800
Glu Ile Val Asn        790                              795
GAA ATA GTA AAT        GTG CCA GGC ACG GGT TCC TTA TGG CCG CTT TCA GCC CAA AGT CCA ATC

805 Glu Pro Asn Arg Cys Ala Pro His Leu Glu Trp Asn Pro Asp Leu Asp 820
Gly Lys Cys Gly        810                              815
GGA AAG TGT GGA        GAA CCG AAT CGA TGC GCG CCA CAC CTT GAA TGG AAT CCT GAT CTA GAT

825 Asp Gly Glu Lys Cys Ala His His Ser His Phe Thr Leu Asp Ile 840
Cys Ser Cys Arg        830                              835
TGT TCC TGC AGA        GAC GGG GAA AAA TGT GCA CAT CAT TCC CAT CAT TTC ACC TTG GAT ATT

845 Thr Asp Leu Asn Glu Asp Leu Gly Val Trp Val Ile Phe Lys Ile Lys 860
Asp Val Gly Cys        850                              855
GAT GTT GGA TGT        ACA GAC TTA AAT GAG GAC TTA GGT GTA TGG GTG ATA TTC AAG ATT AAG

865 Ala Arg Leu Gly Asn Leu Glu Phe Leu Glu Lys Pro Leu Leu 880
Thr Gln Asp Gly His    870                              875
ACG CAA GAT GGC CAT    GCA AGA CTA GGG AAT CTA GAG TTT CTC GAA AAA CCA TTA TTA
```

FIGURE 9-9

```
                885              890              895        900
Gly Glu Ala Leu Arg Val Lys Arg Ala Glu Lys Lys Trp Arg Asp Lys Arg Glu Lys
GGG GAA GCA CTA CGT GTG AAA AGA GCG GAG AAG AAG TGG AGA GAC AAA CGA GAG AAA 905              910              915        920
Leu Gln Leu Glu Thr Asn Ile Val Tyr Lys Glu Ala Lys Glu Ser Val Asp Ala Leu Phe
CTG CAG TTG GAA ACA AAT ATT GTT TAT AAA GAA GCA AAA GAA TCT GTA GAT GCT TTA TTT 925              930              935        940
Val Asn Ser Gln Tyr Asp Arg Leu Gln Val Asp Thr Asn Ile Ala Met Ile His Ala Ala
GTA AAC TCT CAA TAT GAT AGA TTA CAA GTG GAT ACG AAC ATC GCA ATG ATT CAT GCG GCA 945              950              955        960
Asp Lys Arg Val His Arg Ile Arg Glu Ala Tyr Leu Pro Glu Leu Ser Val Ile Pro Gly
GAT AAA CGC GTT CAT AGA ATC CGG GAA TAT CTG CCA GAG TTG TCT GTG ATT CCA GGT 965              970              975        980
Val Asn Ala Ala Ile Phe Glu Glu Leu Glu Gly Arg Ile Phe Thr Ala Tyr Ser Leu Tyr
GTC AAT GCG GCC ATT TTC GAA GAA TTA GAG GGA CGT ATT TTT ACA GCG TAT TCC TTA TAT
```

FIGURE 9-10

```
                  985              990              995              1000
Asp Ala Arg Asn Val Ile Lys Asn Gly Asp Phe Asn Asn Gly Leu Cys Trp Asn Val
GAT GCG AGA AAT GTC ATT AAA AAT GGC GAT TTC AAT AAT GGC TTA TGC TGG AAC GTG
          1005             1010             1015             1020
Lys Gly His Val Asp Val Glu Glu Gln Asn His Arg Ser Val Leu Val Ile Pro Glu
AAA GGT CAT GTA GAT GTA GAA GAG CAA AAC CAC CGT TCG GTC CTT GTT ATC CCA GAA
          1025             1030             1035             1040
Trp Glu Ala Glu Val Ser Gln Glu Val Arg Val Cys Pro Gly Arg Gly Tyr Ile Leu Arg
TGG GAG GCA GAA GTG TCA CAA GAG GTT CGT TGT CCA GGT CGT GGC TAT ATC CTT CGT
          1045             1050             1055             1060
Val Thr Ala Tyr Lys Glu Gly Tyr Gly Glu Gly Cys Val Thr Ile His Glu Ile Glu Asp
GTC ACA GCA TAT AAA GAG GGA TAT GGA GAG GGC TGC GTA ACG ATC CAT GAG ATC GAG GAC
          1065             1070             1075             1080
Asn Thr Asp Glu Leu Lys Phe Ser Asn Cys Val Glu Glu Val Tyr Pro Asn Asn Thr
AAT ACA GAC GAA CTG AAA TTC AGC AAC TGT GTA GAA GAG GTA TAT CCA AAC AAC ACA
```

FIGURE 9-11

```
                                   1085                    1090                    1095                    1100
Val Thr Cys Asn Asn Tyr Thr Gly Thr Gln Glu Glu Tyr Glu Gly Thr Tyr Thr Ser Arg
GTA ACG TGT AAT AAT TAT ACT GGG ACT CAA GAA GAA TAT GAG GGT ACG TAC ACT TCT CGT 1105                    1110                    1115                    1120
Asn Gln Gly Tyr Asp Glu Ala Tyr Gly Asn Asn Pro Ser Val Pro Ala Asp Tyr Ala Ser
AAT CAA GGA TAT GAC GAA GCC TAT GGT AAT AAC CCT TCC GTA CCA GCT TAC GCT TCA 1125                    1130                    1135                    1140
Val Tyr Glu Glu Lys Ser Tyr Thr Asp Gly Arg Arg Glu Asn Pro Cys Glu Ser Asn Arg
GTC TAT GAA GAA AAA TCG TAT ACA GAT GGA CGA AGA GAG AAT CCT TGT GAA TCT AAC AGA 1145                    1150                    1155                    1160
Gly Tyr Gly Asp Tyr Thr Pro Leu Pro Ala Gly Tyr Val Thr Lys Asp Leu Glu Tyr Phe
GGC TAT GGG GAT TAC ACA CCA CTA CCG GCT GGT TAT GTA ACA AAG GAT TTA GAG TAC TTC 1165                    1170                    1175                    1180
Pro Glu Thr Asp Lys Val Trp Ile Glu Ile Gly Glu Thr Gly Thr Phe Ile Val Asp
CCA GAG ACC GAT AAG GTA TGG ATT GAG ATC GGA GAA ACA GGA ACA TTC ATC GTG GAT

1185
Ser Val Glu Leu Leu Leu Met Glu Glu
AGC GTG GAA TTA CTC CTT ATG GAG GAA
```

A. Bacillus thuringiensis HD-1
B. Bacillus thuringiensis P5811

5,126,133

BACILLUS THURINGIENSIS ISOLATE ACTIVE AGAINST LEPIDOPTERAN PESTS, AND GENES ENCODING NOVEL LEPIDOPTERAN-ACTIVE TOXINS

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. *kurstaki* HD-1 produces a crystal inclusion consisting of a biotoxin called a delta toxin which is toxic to the larvae of a number of lepidopteran insects. The cloning, sequencing, and expression of this *B.t.* crystal protein gene in *Escherichia coli* has been described in the published literature (Schnepf, H. E. and Whitely, H. R. [1981] Proc. Natl. Acad. Sci. USA 78:2893–2897; Schnepf et al.). U.S. Pat. Nos. 4,448,885 and 4,467,036 both disclose the expression of *B.t.* crystal protein in *E. coli*.

BRIEF SUMMARY OF THE INVENTION

The subject invention concerns a novel *Bacillus thuringiensis* isolate designated *B.t.* PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel *B.t.* isolate denoted *B.t.* PS81I, mutants thereof, and novel δ-endotoxin genes derived from this *B.t.* isolate which encode proteins which are active against lepidopteran pests.

BRIEF DESCRIPTION OF THE DRAWINGS

FIG. 1-1 to 1-4 Nucleotide Sequence of toxin gene 81IA2.

FIG. 2-1 to 2-5 Deduced amino acid sequence of toxin expressed by toxin gene 81IA2.

FIG. 3-1 to 3-12 Composite of FIGS. 1 and 2.

FIG. 4-1 to 4-4 Nucleotide sequence of the toxin gene 81IB.

FIG. 5-1 to 5-5 Deduced amino acid sequence of toxin expressed by toxin gene 81IB.

FIG. 6-1 to 6-12 Composite of FIGS. 4 and 5.

FIG. 7-1 and 7-4 Nucleotide sequence of the toxin gene 81IB2.

FIG. 8-1 to 8-5 Deduced amino acid sequence of toxin expressed by toxin gene 81IB2.

FIG. 9-1 to 9-12 Composite of FIGS. 7 and 8.

FIG. 10 Agarose gel electrophoresis of plasmid preparation from *B.t.* HD-1 and *B.t.* PS81I.

DETAILED DISCLOSURE OF THE INVENTION

The novel toxin genes of the subject invention were obtained from a novel lepidopteran-active *B. thuringiensis* (*B.t.*) isolate designated PS81I.

Characteristics of *B.t.* PS81I

Colony morphology—Large colony, dull surface, typical *B.t*

Vegetative cell morphology—typical *B.t.*

Flagellar serotype—7, aizawai.

Intracellular inclusions—sporulating cells produce a bipyramidal crystal.

Plasmid preparations—agarose gel electrophoresis of plasmid preparations distinguishing *B.t.* PS81I from *B.t.* HD-1. See FIG. 1.

Alkali-soluble proteins—SDS-PAGE analysis shows a protein band at ca. 130,000 daltons.

Unique toxins—four unique toxins have been identified in *B.t.* PS81I.

Activity—*B.t.* PS81I kills all Lepidoptera tested.

Bioassay procedures:

*B.t.* PS81I spores and crystals were tested against: Beet Armyworm, *Spodoptera exigua;* Diamondback Moth, *Plutella xylostella;* Western Spruce Budworm, *Choristoneura occidentalis.*

LC50 values were as follows:

Beet Armyworm—2.53 ppm
Diamondback Moth—0.16 ppm
Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS81I, and mutants thereof, can be used to control lepidopteran pests.

A subculture of *B.t.* PS81I and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
| --- | --- | --- |
| B.t. PS81I | NRRL B-18484 | April 19, 1989 |
| E. coli (NM522)(pMYC392) | NRRL B-18498 | May 17, 1989 |
| E. coli (NM522)(pMYC393) | NRRL B-18499 | May 17, 1989 |
| E. coli (NM522)(pMYC394) | NRRL B-18500 | May 17, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lost the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp,; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the $B. t.$ insecticidal gene may be grown in any convenient nutrient medium, where the DNA construct provides a selective advantage, providing for a selective medium so that substantially all or all of the cells retain the $B.t.$ gene. These cells may then be harvested in accordance with conventional ways. Alternatively, the cells can be treated prior to harvesting.

The $B.t.$ cells may be formulated in a variety of ways. They may be employed as wettable powders, granules or dusts, by mixing with various inert materials, such as inorganic minerals (phyllosilicates, carbonates, sulfates, phosphates, and the like) or botanical materials )powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS811 can be made by procedures well known in the art. For example, an asporogenous mutant can be obtained through ethylmethane sulfonate (EMS) mutagenesis of PS811. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing $B.t.$ PS811

A subculture of B.t. PS811, or mutants thereof, can be used to inoculate the following medium, a peptone, glucose, salts medium.
Bacto Peptone: 7.5 g/l
Glucose: 1.0 g/l
$KH_2PO_4$: 3.4 g/l
$K_2HOP_4$: 4.35 g/l
Salt Solution: 5.0 ml/l
$CaCl_2$ Solution: 5.0 ml/l
Salts Solution (100 ml)
$MgSO_4.7H_2O$: 2.46 g
$MnSO_4.H_2O$: 0.04 g
$ZnSO_4.7H_2O$: 0.28 g
$FeSO_4.7H_2O$: 0.40 g
$CaCl_2$ Solution (100 ml)
$CaCl_2.2H_2O$: 3.66 g
pH 7.2

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation into *Escherichia coli*

Total cellular DNA was prepared from B.t. cells grown to a low optical density ($OD_{600}=1.0$). The cells were recovered by centrifugation and protoplasted in TES buffer (30 mM Tris-Cl, 10 mM ethylenediaminetegraacetic acid [EDTA], 50 mM NaCl, P=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and *B.t.k.* HD-1 was digested with *Eco*RI and separated by electrophoresis on a 0.8% (w/v) Agarose-TAE (50 mM Tris-Cl, 20 mM NaOAc, 2.5 mM EDTA, PH=8.0) buffered gel. A Southern blot of the gel was hybridized with a [$^{32}$P] radiolabeled probe against the 3.2 Kb *Nsi*I to *Nsi*I fragment of the toxin gene contained in plasmid pM3,130-7 of NRRL B-18332 and the 2.4 Kb *Nsi*I to *Kpn*I fragment of the "4.5 Kb class" toxin gene (Kronstad and Whitely [1986] Gene USA 43:29-40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in coning two of the three *Eco*RI fragments described above. Two hundred micrograms of PS81I total cellular DNA was digested with *Eco*RI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP TM -d (Schleicher and Schuell, Keene, NH) ion exchange column according to the manufacturer's specification. The isolated *Eco*RI fragments were ligated to LAMBDA ZAP TM *Eco*RI arms (Stratagene Cloning Systems, La Jolla, Calif.) and packaged using Gigapak GOLD TM (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb *Eco*RI inserts, respectively. The DNA sequence of both inserts was determined using Stratagene's T7 and T3 oligonucleotide primers plus a set of existing internal *B.t.* endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced *B.t.* endotoxin genes showed that two distinct, unique partial toxin gene sequences had been found. Synthetic oligonucleotides were constructed to regions in both sequences that had minimum homology to other characterized B.t. endotoxin genes. The 42-mer oligonucleotide constructed to the sequence of the insert in pM2,31-4 was GGATACCGGTGACCCATTAACATTCCAATCTTTTAGTTACGC; it was used to isolate a toxin gene sequence called 81IA. The 40mer oligonucleotide constructed to the sequence of the insert in pM2,31-1 was GAAGTTTATGGCCTCTTTCTGTAGAAAATCAAATTGGACC; it was used to isolate a toxin gene sequence called 81IB.

In order to clone both complete toxin genes, a *Sau*3A partial library was constructed. PS81I total cellular DNA partially digested with *Sau*3A and size fractionated by electrophoresis into a mixture of 9-23 Kb fragments on a 0.6% agarose-TAE gel, and purified as described previously, was ligated into LambdaGEM-11 TM (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with *Sal*I (to release the inserted DNA from lambda arms) and separated by electrophoresis on a 0.6% agarose-TAE gel. The large fragments, electroeluted and concentrated as described above, were ligated to *Sal*I-digested and dephosphorylated pUC19 (NEB). The ligation mix was introduced by transformation into DH5(α) competent *E. coli* cells (BRL) and plated on LB agar containing ampicillin, isopropyl-(62)-D-thiogalactoside (IPTG), and 5-bromo- 4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb *Sau*3A fragment isolated using the 81IA oligonucleotide probe. Plasmid pM4,59-1 contains an 18 Kb *Sau*3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known *B.t.k.* toxin genes. The resulting autoradiogram showed that two toxin genes were present in tandem on this cloned *Sau*3A fragment. Plasmid pM3,122-1 had a 4.0 Kb *Nde*I fragment that hybridized with oligonucleotide probes made to known *B.t.k.* genes. This fragment, however, did not hybridize with the specific oligonucleotides to 81IA or 8 IB; a new toxin gene had been discovered and subsequently was called 81IA2. The 4.0 Kb *Nde*I fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603. The 81IA toxin gene is unique based on its restriction map and is presently being sequenced.

Plasmid pm4,59-1 was digested with several restriction enzymes and Southern blotted. The blot was probed with the [$^{32}$P] radiolabeled 81IB specific oligonucleotide probe, as well as with labeled oligonucleotide sequencing primers made to known B.t.k. toxin genes. The plasmid pm4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the next toxin genes. Sequence analysis of three toxin genes has elucidated three unique open reading frames and has deduced three unique endotoxin proteins (FIGS. 1-9). The following table summarizes the size of each ORF in base pairs and the deduced endotoxin molecular weight in daltons.

| TOXIN GENE | ORF (bp) | DEDUCED MW (daltons) | FIGURE |
|---|---|---|---|
| 81IA2 | 3537 | 133,397 | 1–3 |
| 81IB | 3495 | 132,480 | 4–6 |
| 81IB2 | 3567 | 134,714 | 7–9 |

An endotoxin protein has been expressed in Pseudomonas and/or Bacillus from the three cloned and sequenced toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by genes 81IA, 81IB, and 81IB2 expressed in either a Bacillus or Pseudomonas host have activity against all lepidopteran insects tested: Trichoplusia ni, Spondoptera exigua, Plutella xylostells, and Choristoneura occidentalis.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the B.t. toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] *Cell* 32:1033-1043). A particularly useful vector in this regard is pEND4K (Klee, H. J., Yanofsky, M. F. and Nester, E. W. [1985] *Bio/Technology* 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel B. thuringiensis Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol., 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel B.T. toxin genes are shown in FIGS. 1, 4 and 7. The deduced amino acid sequences are shown in FIGS. 2, 5 and 8.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the stand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G is W is A
QR = TC is S is A, G, C or T; alternatively
QR = AG if S is T or C
J = A or G
K = T or C
L = A, T, C or G
M = A, C or T The above shows that the novel amino acids sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequences if such changes do not alter the protein secondary structure (Kaiser, E. T. and Kezdy, F. J. [1984]Science 223:249–225). Thus, the subject invention includes mutants of the amino acid sequence depicted herein which do not alter the protein secondary structure, or if the structure is altered, the biological activity is retained to some degree.

We claim:

1. A process for controlling lepidopteran insect pests which comprises contacting said insect pests with an insect-controlling effective amount of *bacillus thuringiensis*, PS81I, having all the identifying characteristics of NRRL B-18484, or mutants thereof.

2. The process, according to claim 1, wherein said mutants are asporogenous mutants and/or phage resistant mutants.

3. The process, according to claim 1, wherein said insect pest is contacted with an insect-controlling effective amount of *Bacillus thuringiensis* PS81I, by incorporating said *Bacillus thuringiensis* PS 81I into a bait granule and placing said granule on or in the soil when planting seed of a plant upon which plant insect pest is known to feed.

4. A process for controlling soil-inhabiting insect pests of the order Lepidoptera which comprises
   (1) preparing a bait granule comprising *Bacillus thuringiensis* PS81I, or mutants thereof, spores or crystals; and
   (2) placing said bait granule on or in the soil.

5. The process, according to claim 4, wherein said bait granule is applied at the same time corn seed is planted in the soil.

6. The process, according to claim 1 or 4, wherein substantially intact *Bacillus thuringiensis* PS81I cells, or mutants thereof, are treated to prolong the pesticidal activity when the substantially intact cells are applied to the environment of a target pest.

7. A composition of matter comprising *Bacillus thuringiensis* PS81I, or mutants thereof, spores or crystals in association with an insecticide carrier, wherein said mutants are asporogenous mutants and/or phage resistant mutants.

8. The composition of matter, according to claim 7, wherein said carrier comprises phagostimulants or attractants.

9. A composition of matter comprising *Bacillus thuringiensis PS*81I, or mutants thereof, in association with formulation ingredients applied as a seed coating, wherein said mutants are asporogenous mutants and/or phage resistant mutants.

10. *Bacillus thuringiensis* PS81I, having all the identifying characteristics of NRRL B-18484, or mutants thereof, having activity against insect pests of the order Lepidoptera.

11. Asporogenous and/or phage resistant mutants of *Bacillus thuringiensis PS*81I.

* * * * *

UNITED STATES PATENT AND TRADEMARK OFFICE
CERTIFICATE OF CORRECTION

PATENT NO. : 5,126,133

DATED : June 30, 1992

INVENTOR(S) : Jewel M. Payne, et al

Page 1 of 2

It is certified that error appears in the above-indentified patent and that said Letters Patent is hereby corrected as shown below:

| | |
|---|---|
| Column 1, line 36: | "δ-endotoxiin" should read --δ-endotoxin--. |
| Column 2, line 27: | "larvae 4th instar" should read --larvae, 4th instar--. |
| Column 3, line 9: | "finishing" should read --furnishing--. |
| Column 5, line 25: | "lost" should read --lose--. |
| Column 7, line 42: | "materials )powdered" should read --materials (powdered". |
| Column 7, line 54: | "will present" should read --will be present-- |
| Column 8, line 52: | "$K_2HOP_4$" should read --$K_2HPO_4$--. |
| Column 9, line 13: | "ethylenediaminetegraacetic" should read --ethylenediaminetetraacetic--. |
| Column 9, line 14: | "P=8.0" should read --pH=8.0--. |
| Column 9, line 40: | "coning two of" should read --cloning two of--. |
| Column 10, line 17: | "The 40mer" should read --The 40-mer--. |
| Column 10, line 46: | "isopropyl-(62)" should read --isopropyl-($\beta$)--. |
| Column 11, line 8: | "Plasmid pm4,59-1" should read --Plasmid pM4,59-1--. |
| Column 11, line 13: | "plasmid pm4,59-1" should read --plasmid pM4,59-1--. |
| Column 11, line 30: | "the next toxin" should read --the new toxin--. |
| Column 11, line 52: | "*Plutella xylostells*" should read --*Plutella xylostella*--. |

UNITED STATES PATENT AND TRADEMARK OFFICE
CERTIFICATE OF CORRECTION

PATENT NO. : 5,126,133
DATED : June 30, 1992
INVENTOR(S) : Jewel M. Payne, et al It is certified that error appears in the above-indentified patent and that said Letters Patent is hereby corrected as shown below:

Column 13, line 18: "stand whose" should read --strand whose--.
Column 13, line 50: "223: 249-225)" should read --223: 249-255)--
Column 14, line 6: "*bacillus*" should read --*Bacillus*--.
Column 14, line 42: "PS81l" should read --PS81I--.

Signed and Sealed this

Fifth Day of July, 1994

Attest:

BRUCE LEHMAN

Attesting Officer     *Commissioner of Patents and Trademarks*